(12) United States Patent
Sugaya et al.

(10) Patent No.: US 9,127,291 B2
(45) Date of Patent: Sep. 8, 2015

(54) METHODS AND PRODUCTS FOR BIASING CELLULAR DEVELOPMENT

(71) Applicants: Kiminobu Sugaya, Winter Park, FL (US); Angel Alvarez, Chicago, IL (US); Amelia Marutle, Stockholm (SE)

(72) Inventors: Kiminobu Sugaya, Winter Park, FL (US); Angel Alvarez, Chicago, IL (US); Amelia Marutle, Stockholm (SE)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/969,799

(22) Filed: Aug. 19, 2013

(65) Prior Publication Data

US 2015/0056704 A1    Feb. 26, 2015

Related U.S. Application Data

(62) Division of application No. 13/330,957, filed on Dec. 20, 2011, now Pat. No. 8,513,017, which is a division of application No. 11/258,603, filed on Oct. 24, 2005, now Pat. No. 8,080,420.

(60) Provisional application No. 60/621,483, filed on Oct. 22, 2004.

(51) Int. Cl.
    C12N 5/02       (2006.01)
    C12N 15/85      (2006.01)
    C12N 5/077      (2010.01)
    C12N 15/87      (2006.01)

(52) U.S. Cl.
    CPC ............. *C12N 15/85* (2013.01); *C12N 5/0657* (2013.01); *C12N 15/87* (2013.01); *C12N 2501/40* (2013.01); *C12N 2506/08* (2013.01); *C12N 2510/00* (2013.01)

(58) Field of Classification Search
    None
    See application file for complete search history.

(56) References Cited

U.S. PATENT DOCUMENTS

| | | | |
|---|---|---|---|
| 6,787,355 B1 | 9/2004 | Miller et al. | |
| 7,390,659 B2 | 6/2008 | Jessell et al. | |
| 7,618,621 B2 | 11/2009 | Sugaya et al. | |
| 7,635,467 B2 | 12/2009 | Sugaya et al. | |
| 7,687,505 B2 | 3/2010 | Sugaya et al. | |
| 7,736,892 B2 | 6/2010 | Weiss et al. | |
| 2002/0127715 A1 | 9/2002 | Benvenisty et al. | |
| 2003/0175958 A1 | 9/2003 | Reed et al. | |
| 2003/0224411 A1 | 12/2003 | Stanton et al. | |
| 2004/0241854 A1 | 12/2004 | Davidson et al. | |
| 2005/0245475 A1 | 11/2005 | Khvorova et al. | |

OTHER PUBLICATIONS

Molecular and Cellula Neuroscience 17, 671-682, 2001.*
Zheng et al., Overexpression of Math1 induces robust production of extra hair cells in postnatal rat inner ears, Nature Neuroscience, Jun. 2000, vol. 3, No. 6, pp. 580-586.
Helms et al., Overexpression of Math1 Disrupts the Coordination of Neural Differentiation in Cerebellum Development, Molecular and Cellular Neuroscience, 2001, vol. 17 pp. 671-682.
Li et al., Pluripotent stem cells from the adult mouse inner ear, Nature Medicine, Oct. 2003, vol. 9, No. 10, pp. 1293-1299.
Richards et al., Protein stability: still an unsolved problem, Cellular and Molecular Life Sciences, 1997, vol. 53, pp. 790-802.
Warchol et al., Regenerative Proliferation in Inner Ear Sensory Epithelia from Adult Guinea Pigs and Humans, Science, Mar. 1993, vol. 259, pp. 1619-1622.
pRK5 sequence and plasmid map, http://www.addgene.org/pgvec1?f=v&cmd=viewvecseq&from=&soid=5506&view=Draw, Addgene Inc., 2003-2007, downloaded Feb. 27, 2008.
Akazawa et al., A Mammalian Helix-Loop-Helix Factor Structurally Related to the Product of *Drosophila* Proneural Gene atonal is a Positive Transcriptional Regulator Expressed in the Developing Nervous System, The Journal of Biological Chemistry, 1995, vol. 270, No. 15, pp. 8730-8738.
Zhao et al., The LIM-homeobox gene Lhx8 is required for the development of many cholinergic neurons in the mouse forebrain, Proc Natl Acad Sci, Jul. 2003, 100 (15):9005-9010.

* cited by examiner

*Primary Examiner* — Nancy T Vogel
(74) *Attorney, Agent, or Firm* — Timothy H. Van Dyke; Beusse, Wolter, Sanks & Maire, PLLC

(57) ABSTRACT

Methods are described that bias cells, such as potent and multipotent stem cells, by transfection with a nucleic acid sequence, to differentiate to a desired end-stage cell or a cell having characteristics of a desired end-stage cell. In particular embodiments, human neural stem cells are transfected with vectors comprising genes in the homeobox family of transcription factor developmental control genes, and this results in a greater percentage of resultant transformed cells, or their progeny, differentiating into a desired end-stage cell or a cell having characteristics of a desired end-stage cell.

5 Claims, 14 Drawing Sheets

SEQUENCE LISTING

```
<160> NUMBER OF SEQ ID NOS: 23

<210> SEQ ID NO 1
<211> LENGTH: 2144
<212> TYPE: DNA
<213> ORGANISM: Mus musculus

<400> SEQUENCE: 1
tcgacccacg cgtccgccca cgcgtccgga tctccgagtg agaggggag ggtcagagga        60 ggaaggaaaa aaaaatcaga ccttgcagaa gagactagga aggttttttgt tgttgttgtt      120
```

```
cggggcttat cccettcgtt gaactgggtt gccagcacct cctctaacac ggcacctccg      180
agccattgca gtgcgatgtc ccgcctgctg catgcagaag agtgggctga ggtaaaagag      240
ttgggggacc accatcgcca tccccagccg caccacgtcc cgccgctgac gccacagcca      300
cctgctaccc tgcaggcgag agaccttccc gtctacccgg cagaactgtc cctcctggat      360
agcaccgacc cacgcgcctg gctgactccc actttgcagg gcctctgcac ggcacgcgcc      420
gcccagtatc tgctgcattc tcccgagctg ggtgcctccg aggccgcggc gccccgggac      480
gaggctgaca gccagggtga gctggtaagg agaagcggct gtggcggcct cagcaagagc      540
cccgggcccg tcaaagtacg ggaacagctg tgcaagctga agggtggggt tgtagtggac      600
gagcttggct gcagccgcca gcgagcccct tccagcaaac aggtgaatgg ggtacagaag      660
caaaggaggc tggcagcaaa cgcaagggaa cggcgcagga tgcacgggct gaaccacgcc      720
ttcgaccagc tgcgcaacgt tatcccgtcc ttcaacaacg acaagaagct gtccaaatat      780
gagaccctac agatggccca gatctacatc aacgctctgt cggagttgct gcagactccc      840
aatgtcggag agcaaccgcc gccgcccaca gcttcctgca aaaatgacca ccatcacctt      900
cgcaccgcct cctcctatga aggaggtgcg ggcgcctctg cggtagctgg ggctcagcca      960
gccccgggag ggggcccgag acctaccccg cccgggcctt gccggactcg cttctcaggc     1020
ccagcttcct ctgggggtta ctcggtgcag ctggacgctt tgcacttccc agccttcgag     1080
gacagggccc taacagcgat gatggcacag aaggacctgt cgccttcgct gcccgggggc     1140
atcctgcagc ctgtacagga ggacaacagc aaaacatctc ccagatccca cagaagtgac     1200
ggagagtttt ccccccactc tcattacagt gactctgatg aggccagtta ggaaggcaac     1260
agctccctga aaactgagac aaccaaatgc ccttcctagc gcgcgggaag ccccgtgaca     1320
aatatccctg cacccttaa ttttggtct gtggtgatcg ttgttagcaa cgacttgact     1380
tcggacggct gcagctcttc caatccccctt cctcctacct tctccttcct ctgtatgtag     1440
atactgtatc attatatgta cctttacgtg gcatcgtttc atggtccatg ctgccaatat     1500
gctgctaaaa tgtcgtatct ctgcctctgg tctgggtttc acttatttta taccttggga     1560
gttcatcctt gcgtgttgcg ctcactcaca aataagggag ttagtcaatg aagttgtttc     1620
cccaactgct tgagacccgc attgggtact ttactgaaca cggactattg tgttgttaaa     1680
atgcaggggc agataagagt atctgtagag cttagacacc aagtgtgtcc agcagtgtgt     1740
ctagcggacc cagaatacac gcacttcatc actggccgct gcgccgcctt gaagaaactc     1800
aactgccaat gcagagcaac ttttgatttt aaaaacagcc actcataatc attaaactct     1860
ttgcaaatgt ttgtttttgc aaatgaaaat taaaaaaaaa catgtagtgt caaaggcatt     1920
tggtcaattt tattttgctt tgttaacatt agaaagtta tttattattg cgtatttgga     1980
cccatttcta cttaattgcc ttttttttac attttctact cgagatcgtt ttattttgat     2040
ttagcaaatc cagttgccat tgctttatgt atgtatgctc ttttacaaat gataaaataa     2100
actcggaaaa aaaaaaaaa aaaaaaaaa aaaaaaaaa aaaa                          2144
```

<210> SEQ ID NO 2
<211> LENGTH: 2118
<212> TYPE: DNA
<213> ORGANISM: Mus musculus

<400> SEQUENCE: 2

```
acctggtgtg cgatctccga gtgagagggg gagggtcaga ggaggaagga aaaaaaatca       60
gaccttgcag aagagactag gaaggttttt gttgttgttg ttcggggctt atccccttcg      120
```

```
ttgaactggg ttgccagcac ctcctctaac acggcacctc cgagccattg cagtgcgatg      180
tcccgcctgc tgcatgcaga agagtgggct gaggtaaaag agttggggga ccaccatcgc      240
catccccagc cgcaccacgt cccgccgctg acgccacagc cacctgctac cctgcaggcg      300
agagaccttc ccgtctaccc ggcagaactg tccctcctgg atagcaccga cccacgcgcc      360
tggctgactc ccactttgca gggcctctgc acggcacgcg ccgcccagta tctgctgcat      420
tctcccgagc tgggtgcctc cgaggccgcg gcgccccggg acgaggctga cagccagggt      480
gagctggtaa ggagaagcgg ctgtggcggc ctcagcaaga gccccgggcc cgtcaaagta      540
cgggaacagc tgtgcaagct gaaggtgggg gttgtagtgg acgagcttgg ctgcagccgc      600
cagcgagccc cttccagcaa acaggtgaat ggggtacaga agcaaaggag gctggcagca      660
aacgcaaggg aacggcgcag gatgcacggg ctgaaccacg ccttcgacca gctgcgcaac      720
gttatcccgt ccttcaacaa cgacaagaag ctgtccaaat atgagaccct acagatggcc      780
cagatctaca tcaacgctct gtcggagttg ctgcagactc ccaatgtcgg agagcaaccg      840
ccgccgccca cagcttcctg caaaaatgac caccatcacc ttcgcaccgc ctcctcctat      900
gaaggaggtg cgggcgcctc tgcggtagct ggggctcagc cagccccggg aggggcccg      960 agacctaccc cgcccgggcc ttgccggact cgcttctcag gcccagcttc ctctgggggt     1020
tactcggtgc agctggacgc tttgcacttc ccagccttcg aggacagggc cctaacagcg     1080
atgatggcac agaaggacct gtcgccttcg ctgcccgggg gcatcctgca gcctgtacag     1140
gaggacaaca gcaaaacatc tcccagatcc cacagaagtg acggagagtt ttccccccac     1200
tctcattaca gtgactctga tgaggccagt taggaaggca acagctccct gaaaactgag     1260
acaaccaaat gcccttccta gcgcgcggga agccccgtga caaatatccc tgcacccttt     1320 aattttggt ctgtggtgat cgttgttagc aacgacttga cttcggacgg ctgcagctct     1380
tccaatcccc ttcctcctac cttctccttc ctctgtatgt agatactgta tcattatatg     1440
tacctttacg tggcatcgtt tcatggtcca tgctgccaat atgctgctaa aatgtcgtat     1500
ctctgcctct ggtctgggtt tcacttattt tataccttgg gagttcatcc ttgcgtgttg     1560
cgctcactca caaataaggg agttagtcaa tgaagttgtt tccccaactg cttgagaccc     1620
gcattgggta ctttactgaa cacggactat tgtgttgtta aaatgcaggg gcagataaga     1680
gtatctgtag agcttagaca ccaagtgtgt ccagcagtgt gtctagcgga cccagaatac     1740
acgcacttca tcactggccg ctgcgccgcc ttgaagaaac tcaactgcca atgcagagca     1800
acttttgatt ttaaaaacag ccactcataa tcattaaact ctttgcaaat gtttgttttt     1860
gcaaatgaaa attaaaaaaa aacatgtagt gtcaaaggca tttggtcaat tttatttgc     1920 tttgttaaca ttagaaaagt tatttattat tgcgtatttg gacccatttc tacttaattg     1980 ccttttttt acattttcta ctcgagatcg ttttattttg atttagcaaa tccagttgcc     2040
attgctttat gtatgtatgc tcttttacaa atgataaaat aaactcggaa aaaaaaaaa     2100 aaaaaaaaa aaaaaaaa                                                    2118
```

<210> SEQ ID NO 3
<211> LENGTH: 2144
<212> TYPE: DNA
<213> ORGANISM: Mus musculus

<400> SEQUENCE: 3

```
tcgacccacg cgtccgccca cgcgtccgga tctccgagtg agaggggag ggtcagagga       60
```

```
ggaaggaaaa aaaaatcaga ccttgcagaa gagactagga aggtttttgt tgttgttgtt      120
cggggcttat cccettcgtt gaactgggtt gccagcacct cctctaacac ggcacctccg      180
agccattgca gtgcgatgtc ccgcctgctg catgcagaag agtgggctga ggtaaaagag      240
ttggggacc  accatcgcca tccccagccg caccacgtcc cgccgctgac gccacagcca      300
cctgctaccc tgcaggcgag agaccttccc gtctacccgg cagaactgtc cctcctggat      360
agcaccgacc cacgcgcctg gctgactccc actttgcagg gcctctgcac ggcacgcgcc      420
gcccagtatc tgctgcattc tcccgagctg ggtgcctccg aggccgcggc gccccgggac      480
gaggctgaca gccagggtga gctggtaagg agaagcggct gtgcggcct cagcaagagc       540
cccgggcccg tcaaagtacg ggaacagctg tgcaagctga agggtggggt tgtagtggac      600
gagcttggct gcagccgcca gcgagcccct tccagcaaac aggtgaatgg ggtacagaag      660
caaaggaggc tggcagcaaa cgcaagggaa cggcgcagga tgcacgggct gaaccacgcc      720
ttcgaccagc tgcgcaacgt tatcccgtcc ttcaacaacg acaagaagct gtccaaatat      780
gagaccctac agatggccca gatctacatc aacgctctgt cggagttgct gcagactccc      840
aatgtcggag agcaaccgcc gccgcccaca gcttcctgca aaaatgacca ccatcacctt      900
cgcaccgcct cctcctatga aggaggtgcg ggcgcctctg cggtagctgg ggctcagcca      960
gccccgggag gggcccgag acctaccccg cccgggcctt gccggactcg cttctcaggc      1020
ccagcttcct ctgggggtta ctcggtgcag ctggacgctt tgcacttccc agccttcgag    1080
gacagggccc taacagcgat gatggcacag aaggacctgt cgccttcgct gcccgggggc   1140
atcctgcagc ctgtacagga ggacaacagc aaaacatctc ccagatccca cagaagtgac   1200
ggagagtttt ccccccactc tcattacagt gactctgatg aggccagtta ggaaggcaac    1260
agctccctga aaactgagac aaccaaatgc ccttcctagc gcgcgggaag ccccgtgaca    1320
aatatccctg cacccttt aa ttttt ggtct gtggtgatcg ttgttagcaa cgacttgact 1380
tcggacggct gcagctcttc caatccccctt cctcctacct tctccttcct ctgtatgtag   1440
atactgtatc attatatgta cctttacgtg gcatcgtttc atggtccatg ctgccaatat   1500
gctgctaaaa tgtcgtatct ctgcctctgg tctgggtttc acttatttta taccttggga    1560
gttcatcctt gcgtgttgcg ctcactcaca aataagggag ttagtcaatg aagttgtttc   1620
cccaactgct tgagacccgc attgggtact ttactgaaca cggactattg tgttgttaaa    1680
atgcaggggc agataagagt atctgtagag cttagacacc aagtgtgtcc agcagtgtgt   1740
ctagcggacc cagaatacac gcacttcatc actggccgct gcgccgcctt gaagaaactc    1800
aactgccaat gcagagcaac ttttgatttt aaaaacagcc actcataatc attaaactct    1860
ttgcaaatgt ttgtttttgc aaatgaaaat taaaaaaaaa catgtagtgt caaaggcatt    1920
tggtcaattt tattttgctt tgttaacatt agaaaagtta tttattattg cgtatttgga   1980
cccatttcta cttaattgcc ttttttttac attttctact cgagatcgtt ttattttgat   2040
ttagcaaatc cagttgccat tgctttatgt atgtatgctc ttttacaaat gataaaataa   2100
actcggaaaa aaaaaaaaa aaaaaaaaa aaaaaaaaa aaaa                         2144
```

<210> SEQ ID NO 4
<211> LENGTH: 1572
<212> TYPE: DNA
<213> ORGANISM: Homo sapiens
<220> FEATURE:
<221> NAME/KEY: modified_base
<222> LOCATION: (1497)..(1497)
<223> OTHER INFORMATION: a, c, g, t, unknown or other

```
<220> FEATURE:
<221> NAME/KEY: modified_base
<222> LOCATION: (1504)..(1504)
<223> OTHER INFORMATION: a, c, g, t, unknown or other
<220> FEATURE:
<221> NAME/KEY: modified_base
<222> LOCATION: (1526)..(1526)
<223> OTHER INFORMATION: a, c, g, t, unknown or other
<220> FEATURE:
<221> NAME/KEY: modified_base
<222> LOCATION: (1564)..(1564)
<223> OTHER INFORMATION: a, c, g, t, unknown or other

<400> SEQUENCE: 4
gtcctctgca cacaagaact tttctcgggg tgtaaaaact ctttgattgg ctgctcgcac      60
gcgcctgccc gcgccctcca ttggctgaga agacacgcga ccggcgcgag gaggggggttg    120
ggagaggagc gggggagac tgagtggcgc gtgccgcttt ttaaagggc gcagcgcctt       180
cagcaaccgg agaagcatag ttgcacgcga cctggtgtgt gatctccgag tgggtggggg    240
agggtcgagg agggaaaaaa aaataagacg ttgcagaaga gacccggaaa gggccttttt    300
tttggttgag ctggtgtccc agtgctgcct ccgatcctga gcgtccgagc ctttgcagtg    360
caatgtcccg cctgctgcat gcagaagagt gggctgaagt gaaggagttg ggagaccacc    420
atcgccagcc ccagccgcat catctcccgc aaccgccgcc gccgccgcag ccacctgcaa    480
ctttgcaggc gagagagcat cccgtctacc cgcctgagct gtccctcctg gacagcaccg    540
acccacgcgc ctggctggct cccactttgc agggcatctg cacggcacgc gccgcccagt    600
atttgctaca ttccccggag ctgggtgcct cagaggccgc tgcgcccggg gacgaggtgg    660
acggccgggg ggagctggta aggaggagca gcggcggtgc cagcagcagc aagagccccg    720
ggccggtgaa agtgcgggaa cagctgtgca agctgaaagg cggggtggtg gtagacgagc    780
tgggctgcag ccgccaacgg gccccttcca gcaaacaggt gaatgggtg cagaagcaga    840
gacggctagc agccaacgcc agggagcggc gcaggatgca tgggctgaac cacgccttcg    900
accagctgcg caatgttatc ccgtcgttca acaacgacaa gaagctgtcc aaatatgaga    960
ccctgcagat ggcccaaatc tacatcaacg ccttgtccga gctgctacaa acgcccagcg   1020
gaggggaaca gccaccgccg cctccagcct cctgcaaaag cgaccaccac caccttcgca   1080
ccgcggcctc ctatgaaggg ggcgcgggca acgcgaccgc agctgggct cagcaggctt    1140
ccggagggag ccagccggccg accccgcccg ggagttgccg gactcgcttc tcagccccag   1200
cttctgcggg agggtactcg gtgcagctgg acgctctgca cttctcgact ttcgaggaca   1260
gcgccctgac agcgatgatg gcgcaaaaga atttgtctcc ttctctcccc gggagcatct   1320
tgcagccagt gcaggaggaa aacagcaaaa cttcgcctcg gtcccacaga agcgacgggg   1380
aattttcccc ccattcccat tacagtgact cggatgaggc aagttaggaa ggtgacagaa   1440
gcctgaaaac tgagacagaa acaaaactgc cctttcccag tgcgcgggaa gccccgnggt   1500
taangatccc cgcaccctt aatttnggct ctgcgatggt cgttgtttag caacgacttg   1560
gctncagatg gt                                                        1572

<210> SEQ ID NO 5
<211> LENGTH: 1065
<212> TYPE: DNA
<213> ORGANISM: Homo sapiens

<400> SEQUENCE: 5
atgtcccgcc tgctgcatgc agaagagtgg gctgaagtga aggagttggg agaccaccat     60
```

| | |
|---|---|
| cgccagcccc agccgcatca tctcccgcaa ccgccgccgc cgccgcagcc acctgcaact | 120 |
| ttgcaggcga gagagcatcc cgtctacccg cctgagctgt ccctcctgga cagcaccgac | 180 |
| ccacgcgcct ggctggctcc cactttgcag ggcatctgca cggcacgcgc cgcccagtat | 240 |
| ttgctacatt ccccggagct gggtgcctca gaggccgctg cgccccggga cgaggtggac | 300 |
| ggccggggg agctggtaag gaggagcagc ggcggtgcca gcagcagcaa gagcccgg | 360 |
| ccggtgaaag tgcgggaaca gctgtgcaag ctgaaaggcg gggtggtggt agacgagctg | 420 |
| ggctgcagcc gccaacgggc cccttccagc aaacaggtga atggggtgca gaagcagaga | 480 |
| cggctagcag ccaacgccag ggagcggcgc aggatgcatg gctgaaccca cgccttcgac | 540 |
| cagctgcgca atgttatccc gtcgttcaac aacgacaaga gctgtccaa atatgagacc | 600 |
| ctgcagatgg cccaaatcta catcaacgcc ttgtccgagc tgctacaaac gcccagcgga | 660 |
| ggggaacagc caccgccgcc tccagcctcc tgcaaaagcg accaccacca ccttcgcacc | 720 |
| gcggcctcct atgaaggggg cgcgggcaac gcgaccgcag ctgggctca gcaggcttcc | 780 |
| ggagggagcc agcggccgac cccgcccggg agttgccgga ctcgcttctc agccccagct | 840 |
| tctgcgggag ggtactcggt gcagctggac gctctgcact tctcgacttt cgaggacagc | 900 |
| gccctgacag cgatgatggc gcaaaagaat ttgtctcctt ctctcccgg gagcatcttg | 960 |
| cagccagtgc aggaggaaaa cagcaaaact tcgcctcggt cccacagaag cgacggaa | 1020 |
| ttttcccccc attcccatta cagtgactcg gatgaggcaa gttag | 1065 |

<210> SEQ ID NO 6
<211> LENGTH: 2393
<212> TYPE: DNA
<213> ORGANISM: Homo sapiens

<400> SEQUENCE: 6

| | |
|---|---|
| agaggcaaga ggctagcggc tggaccactt gtgctggagt ggtaaagaac tatcatgaat | 60 |
| ccatttactg aaagtgtcca tttctgaact caccctaaag aggacaaaca ccgcaaagta | 120 |
| gttaaaagtc aggcattcgc gtcggacgtc tgggtttgaa ttctgccctg gcttgactgg | 180 |
| aaacgcttcc cctatttctt ccgtagcgga ccgggagagc ttactggcgc tctgcgaacc | 240 |
| ggctggaaag aaacaccgag tcactcgtac agactcttgg tcgcagaact tggctttccg | 300 |
| ctattggtcc tccagaaccg cttgaaacaa ctggccccag ctggcgcatc agaccgcagt | 360 |
| gaggaatgcc gcggggcggg tggcgaaggc agggtctgcc cgccagtgga ttcccgggtg | 420 |
| tcccgcgtgg agcaggcttg cccagctggg aagcccatca acctcagtc ttggcccaca | 480 |
| gtgggagaga gaccagtggg tcccagacgg aggccctcgc ccgcttttgg cgacctccac | 540 |
| tggcgtgaat aaaagcaccc ctctcttacc ctcagaaact gtgggtagca aggtataaaa | 600 |
| cggagtctgg gaccggtaag tcccaaggtg agcccgtata cagctctgcc atctctgagg | 660 |
| ggttatgcag attctgagca ggtgtcaggg gctcatgtca gaggagtgcg gcggactac | 720 |
| agccctggcg gccgggagga ctcgcaaagg cgccggggaa gagggactgg tgagccccga | 780 |
| gggagcgggg gacgaggact cgtgctcctc ctcggccccg ctgtccccgt cgtcctcgcc | 840 |
| ccggtccatg gcctcgggct ccggctgccc tcctggcaag tgtgtgtgca acagttgcgg | 900 |
| cctggagatc gtggacaaat accttctcaa ggtgaatgac ctatgctggc atgtccggtg | 960 |
| tctctcctgc agtgttttgca gaacctcccct aggaaggcac accagctgtt atattaaaga | 1020 |
| caaagacatt ttctgcaaac ttgattattt cagaaggtat ggaactcgct gctctcgatg | 1080 |
| tgggagacac atccattcta ctgactgggt ccggagagcc aaggggaatg tctatcactt | 1140 |

```
ggcatgcttt gcctgctttt cctgcaaaag gcaactttcc acaggagagg agtttgcttt    1200
ggtggaagag aaagtcctct gcagagtaca ttatgactgc atgctggata atttaaaaag    1260
agaagtagaa aatgggaatg ggattagtgt ggaaggtgcc ctcctcacag agcaagatgt    1320
taaccatcca aaaccagcaa aaagagctcg gaccagcttt acagcagatc agcttcaggt    1380
tatgcaagca caatttgctc aggacaacaa cccagatgca cagacactcc agaaattggc    1440
agaaaggaca ggcttgagca gacgtgtgat acaggtgtgg tttcagaatt gtagagcacg    1500
ccacaagaaa cacgtcagtc ctaatcactc atcctccacc ccagtcacag cagtcccacc    1560
ctccaggctg tctccaccca tgttagaaga aatggcttat tctgcctacg tgccccaaga    1620
tggaacgatg ttaactgcgc tgcatagtta tatggatgct cattccacca caactcttgg    1680
actccagccc ttgttacccc attcaatgac acaactgcca ataagtcata cctaattctt    1740
ttttcaggga tagacttgat taaggatata aatttgtcat ttattatgta taaaatacca    1800
ttgaaaagat attactgtta attttttatt taacacctaa agcatttcca acatcacttt    1860
gctgcccagg tatgtatcta tagttggcct gcaagacact tttattaatt cttcattttt    1920
tgtaaaactt atgtttacaa gaagaaaaca aatcaaaaca ttttttgtat tgtctggaaa    1980
tagttcactc tagtgtgtat ctgttaattt atttgtcatc aaaagagcac tttgcctaaa    2040
agaaaggact gacaagtgtg caaaatgttt acaatctttt gtgaaattgt agtttatcat    2100
tagtttgtat ctgtaagtta ttgtaataaa tattacctgt attttttgtt atatacaact    2160
ttatactttg aagcttgtat ctgtgaattt gcaactgaaa tttattttgc caatgttttc    2220
tgaatgaact gaataaagct tctgttgtag catgccatgc aaacacatta ttgtgtttgt    2280
ggttgatgaa ttatggctgt aaataacact atagtttaat aagcccacca ttctgagttt    2340
attaaacatt ttccattctt gtgaaaattt caaaaaaaaa aaaaaaaaaa aaa          2393

<210> SEQ ID NO 7
<211> LENGTH: 1500
<212> TYPE: DNA
<213> ORGANISM: Mus musculus

<400> SEQUENCE: 7
gaattcggca cgagcttcag gaaaagactt ttccccccac tcccctcct ctctgcgagg      60 ttccaccctc tggaaaacac aactttccct cttttctgg agggacaggc cttagtgtgg     120
ctgagagagg aagaacagtg ggtcagagag tggttacgtc actgtggcct ttttggaaca    180
agacacactg gtggcatcgc tgtcctgcct gttagctttc cttggccttt ggggcggag     240 gaggggacac tgcggacacc cacagcctct gaccctgctg gagctggtat gtgacgagca    300
gccctcgggc catgtattgg aagagcgatc agatgtttgt gtgtaagctg gagggaaagg    360
agatgccgga gctggcggtt ccccgcgaga tgtgccccgg gctcatgtcg gaggagtgcg    420 gcggcctgc agctggcgcc gggaggaccc gcaaaggctc tggggaagaa ggactggtga    480
atcccgaggg agccggggac gaggactcct gctcctcctc gggcccgctt tcccgtcgt    540 cctcgcccca gtccatggcc tcgggtccga tgtgcccgcc aggcaagtgt gtgtgcagca    600
gctgcggcct ggagattgtg gacaaatacc tcctcaaggt gaatgactta tgctggcatg    660
tccgctgtct ctcctgcagt gtctgcagaa cgtccctggg aaggcacacg agctgctaca    720
ttaaggataa agatattttc tgtaaactcg attacttcag acggtatggg accgctgtt    780 cccgctgtgg caggcacatc cactcgactg actgggtccg cagggcaaag ggcaacgtgt    840
```

```
atcacctggc ctgctttgcc tgcttttctt gcaagaggca gctgtccacg ggagaggagt    900
tcgccttggt ggaggagaag gtcctctgta gagtgcactt tgactgcatg ctggacaatc    960
tgaagagaga agtggagaac ggtaatggga ttagtgtgga aggagcccctt ctcacagagc   1020 aagacgtcaa tcatccaaag ccagccaaaa gagctcggac cagcttcaca gccgatcagc   1080
tccaggttat gcaagcacag ttcgctcagg acaacaaccc agatgcacag accctccaga   1140
aactggcaga aggacaggc ttaagcagac gtgtcataca ggtgtggttt cagaactgca   1200
gggcccgcca taagaaacac gtcagcccaa accattcttc ctcggccccc gtcacagctg   1260 tccccctcctc caggctgtcc ccacccatct tggaagaaat ggcttattct gcctacgacc   1320
cccaggatga cgggatgctg actgcgcact catacttgga tgctcaccaa caactcctgg   1380
actccagccc ttgttacccc atccaatgac ccagctgcca ataagtcata cctaattcct   1440
tctttcaggg atagaaatga ttgaggttat aaacttgtca ttttattatg tataaaaata   1500

<210> SEQ ID NO 8
<211> LENGTH: 751
<212> TYPE: DNA
<213> ORGANISM: Mus musculus

<400> SEQUENCE: 8
tgttttgtag ctcaccaaca actcctggac tccagcccttt gttacccccat ccaatgaccc    60 agctgccaat aagtcatacc taattccttc tttcagggat agaaatgatt gaggttataa   120
acttgtcatt tattatgtat aaaataccat tgagaagata ttaatgttaa ttttttattt   180
aacactcaaa gcatttcgaa catcctctcg ctgcccaggt atgtatctag agttggcctg   240
caagacactt ttattgattc ttcattttgg tttttttttg taaaacttat gtttacaaag   300
aagaaaacaa gtcaaaacat ttttttttgt attgtctgga gatagttggc tcgagtgtgt   360
gtctattaac ttatttgtca ccaaaagagc actttgcctg aaaggcagga ctgatcgtgt   420
gcaaaacgtt tacaatcctt tgtgaaactg tagtttatca ttagtttgta cctgtaagtt   480
attgttataa atattatctg tattttttgt catatacaac tttataccctt gaagcttgta   540 tctgtgaatt tgcaactgaa atttattttg ccagtgtttt cgggacaagc tgaaggcacg   600
tccgttgtag catgccgcgc acccacgg ggtgcctgca cttggagttc agctgtaaa    660 taacactcta gttacaaag cctaccatcc taagttcatt aaacactttg catccttgtg   720
aaagttgctg cccacttctc ttctgtgtgt a    751

<210> SEQ ID NO 9
<211> LENGTH: 1452
<212> TYPE: DNA
<213> ORGANISM: Mus musculus

<400> SEQUENCE: 9
ggagcaagtg aagcgtaatt tgaggaagat ggatgagtcc ggagggcgac accccccaacc    60 cgcccgcccg ccccctcccct ccttatgagc gagagagcgc ggcgcggag ccacactgcg   120 cagagcccgc gccccgccgc cacctcggcc cgcgcgcccg cagcgagcca tgcgtgtccg   180
cgcggggcgc acgcgggc ccggcagcg ccatgcagag agcggcaggc ggcggcgccc   240 ccggggggcag cggcgggagc agcggcggcc ccggcgccgc cttctccatc gactcgctca   300
tcgggccgcc gccgccgcgc tcgggccacc tgctctacac cggctacccc atgttcatgc   360
cctaccggcc gctcgtgttg ccgcaggcgc tggccccgc gccgctgccc gcggcctgc   420 cgccgctcgc cccgctcgcc tcgttcgccg gccgcctgag caataccttc tgcgcggggc   480
```

```
tgggccaggc ggtgccctcg atggtggcgc tgaccactgc gctgcccagc ttcgcagagc      540
ccccggacgc tactacggg ccccggagc tcgccgccgc cgccgcctcc accgcctcgc       600
gaagcaaccc ggagcccgcg gcccggcgca ctgacggagc gctggacgct gaggagctgc      660
tgcccgcgcg cgagaaagtg actgaacctc cgccgccccc gcctccgcac ttctctgaga      720
ctttcccgag tctaccggca gaggggaagg tgtacagctc agatgaagag aagctagagc      780
ccccagcagg agacccagca ggcagcgagc aggaggaaga gggctcaggc ggtgacagcg      840
aggacagctt cctggacagt tctgcagggg gcccaggggc tcttctggga cctaaaccga      900
agctaaaggg aagcccgggg actggcgctg aggagggac accagtggcc acaggggtca      960
ccacgcctgg ggggaaaagc cgaaggcggc gcacagcctt caccagcgag cagcttttgg     1020
agctggagaa ggagtttcac tgcaagaaat acctgagtct gacagagcgc tcccagatcg     1080
cccacgccct caagctcagt gaggtgcagg tgaagatctg gtttcagaac cgccgggcca     1140
agtggaagcg catcaaggct ggcaatgtga gcagtcgttc tggggagccg gtgagaaacc     1200
ccaagattgt agtgcccata cctgtgcacg tcaacaggtt tgctgtgcgc agccagcacc     1260
aacagatgga gcaaggagcc cggccctgac cgagctcccc ggaccggaag tcacaggatc     1320
tgaacctgtg gccgccaag actcactggg tactgcagcc tagaggggcc tgttgaaccc     1380
tgctccggga gaggccagcg tattcccggg acacaagact atttggcctg agactgttct     1440
agagacctca gg                                                        1452

<210> SEQ ID NO 10
<211> LENGTH: 1632
<212> TYPE: DNA
<213> ORGANISM: Homo sapiens

<400> SEQUENCE: 10
gacgggtgcg cgggcgggcg gcggcaccat gcagggaagc tgccaggggc cgtgggcagc       60
gccgctttct gccgcccacc tggcgctgtg agactggcgc tgccaccatg ttccccagcc      120
ctgctctcac gccacgccc ttctcagtca aagacatcct aaacctggaa cagcagcagc       180
gcagcctggc tgccgccgga gagctctctg cccgcctgga ggcgaccctg cgccctcct       240 cctgcatgct ggccgccttc aagccagagg cctacgctgg gcccgaggcg gctgcgccgg      300
gcctcccaga gctgcgcgca gagctgggcc gcgcgcttc accggccaag tgtgcgtctg      360
cctttcccgc cgccccgcc ttctatccac gtgcctacag cgaccccgac ccagccaagg      420 acctagagc cgaaaagaaa gagctgtgcg cgctgcagaa ggcggtggag ctggagaaga      480
cagaggcgga caacgcggag cggccccggg cgcgacggcg gaggaagccg cgcgtgctct     540
tctcgcaggc gcaggtctat gagctggagc ggcgcttcaa gcagcagcgg tacctgtcgg      600
cccccgaacg cgaccagctg gccagcgtgc tgaaactcac gtccacgcag gtcaagatct     660
ggttccagaa ccgcgctac aagtgcaagc ggcagcggca ggaccagact ctggagctgg      720
tggggctgcc cccgccgccg ccgccgcctg cccgcaggat cgcggtgcca gtgctggtgc      780
gcgatggcaa gccatgccta ggggactcgg cgccctacgc gcctgcctac ggcgtgggcc      840
tcaatcccta cggttataac gcctaccccg cctatccggg ttacggcggc gcggcctgca      900
gccctggcta cagctgcact gccgcttacc ccgccgggcc ttcccagcg cagccggcca     960 ctgccgccgc caacaacaac ttcgtgaact tcgcgtcgg ggacttgaat gcggttcaga     1020
gccccgggat tccgcagagc aactcgggag tgtccacgct gcatggtatc cgagcctggt     1080
```

| | | | |
|---|---|---|---|
| agggaaggga | cccgcgtggc | gcgaccctga | ccgatcccac ctcaacagct ccctgactct | 1140 |
| cgggggggaga | aggggctccc | aacatgaccc | tgagtcccct ggattttgca ttcactcctg | 1200 |
| cggagaccta | ggaactttt | ctgtcccacg | cgcgtttgtt cttgcgcacg ggagagtttg | 1260 |
| tggcggcgat | tatgcagcgt | gcaatgagtg | atcctgcagc ctggtgtctt agctgtcccc | 1320 |
| ccaggagtgc | cctccgagag | tccatgggca | ccccggttg gaactgggac tgagctcggg | 1380 |
| cacgcagggc | ctgagatctg | gccgcccatt | ccgcgagcca gggccgggcg cccgggcctt | 1440 |
| tgctatctcg | ccgtcgcccg | cccacgcacc | cacccgtatt tatgttttta cctattgctg | 1500 |
| taagaaatga | cgatcccctt | cccattaaag | agagtgcgtt gaaaaaaaaa aaaaaaaaa | 1560 |
| aaaaaaaaaa | aaaaaaaaa | aaaaaaaaa | aaaaaaaaa aaaaaaaaa aaaaaaaaa | 1620 |
| aaaaaaaaaa | aa | | | 1632 |

<210> SEQ ID NO 11
<211> LENGTH: 1406
<212> TYPE: DNA
<213> ORGANISM: Homo sapiens

<400> SEQUENCE: 11

| | | | |
|---|---|---|---|
| gagcgcccga | gcggagaggc | ggcccgggag | caggggggcg gcccccactc cggccgggtg | 60 |
| cccggcccct | ggccctgcc | tgccctctag | atcgccgccg cagccgccgc tactgggagt | 120 |
| ctgcctgttg | caggacgcac | tagccctccc | tccatggagt tcggcctgct cagcgaggca | 180 |
| gaggcccgga | gccctgccct | gtcgctgtca | gacgctggca ctccgcaccc ccagctccca | 240 |
| gagcacggct | gcaagggcca | ggagcacagc | gactcagaaa aggcctcggc ttcgctgccc | 300 |
| ggcggctccc | cagaggacgg | ttcgctgaaa | agaagcagc ggcggcagcg cacgcacttc | 360 |
| accagccagc | agctacagga | gctagaggcg | accttccaga ggaaccgcta ccccgacatg | 420 |
| agcacgcgcg | aggagattgc | cgtgtggacc | aacctcaccg aggcccgcgt gcgggtgtgg | 480 |
| ttcaagaacc | ggcgcgccaa | atggcggaag | cgcgagcgca gccagcaggc cgagctatgc | 540 |
| aaaggcagct | tcgcggcgcc | gctcggggg | ctggtgccgc cctacgagga ggtgtacccc | 600 |
| ggctactcgt | acggcaactg | gccgcccaag | gctcttgccc cgccgctcgc cgccaagacc | 660 |
| tttccattcg | ccttcaactc | ggtcaacgtg | gggcctctgg cttcgcagcc cgtcttctcg | 720 |
| ccacccagct | ccatcgccgc | ctccatggtg | ccctccgccg cggctgcccc gggcaccgtg | 780 |
| ccagggcctg | gggcctgca | gggcctgggc | ggggccccc ccgggctggc tccggccgcc | 840 |
| gtgtcctccg | gggccgtgtc | ctgcccttat | gcctcggccg ccgccgccgc cgcggctgcc | 900 |
| gcctcttccc | cctacgtcta | tcgggacccg | tgtaactcga gcctggccag cctgcggctc | 960 |
| aaagccaaac | agcacgcctc | cttcagctac | cccgctgtgc acgggccgcc ccggcagcc | 1020 |
| aaccttagtc | cgtgccagta | cgccgtggaa | aggcccgtat gagcggcccc gcccgtagat | 1080 |
| catccccgag | ggcgggggca | acgattcaca | gcctccgcgg actggggtca ttttgactgg | 1140 |
| cttgctcccg | ccccagggtc | tgaaaggggt | gtttgggcag ctggggggca ccggctcagg | 1200 |
| agagggcctt | cccctcccag | ccctgagggg | tggactaggc cctacacaca gaccgcgccc | 1260 |
| ctgggactaa | agccaggaac | agggaccagc | tccccgggg ccaactcacc cttggcccat | 1320 |
| cccgccttct | ccaggcttcc | cctccctcgt | tttcaaagat aaatgaaata aacgtgcgcg | 1380 |
| gactgtcaaa | aaaaaaaaa | aaaaaa | | 1406 |

<210> SEQ ID NO 12
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgctggcatg tccgctgtct                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctggctttgg atgattgacg                                                    20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccgatcctg agcgtccgag cctt                                               24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcttctgtca ccttcctaac ttgcc                                              25

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
1               5

<210> SEQ ID NO 17
<211> LENGTH: 94
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
tacaagtccg gactcagatc tcgagctcaa gcttcgaatt ctgcagtcga cggtaccgcg        60
ggcccgggat ccaccggatc tagataactg atca                                    94
```

<210> SEQ ID NO 18
<211> LENGTH: 351
<212> TYPE: PRT
<213> ORGANISM: Mus musculus

<400> SEQUENCE: 18

Met Ser Arg Leu Leu His Ala Glu Glu Trp Ala Glu Val Lys Glu Leu
1               5                   10                  15

Gly Asp His His Arg His Pro Gln Pro His His Val Pro Pro Leu Thr
            20                  25                  30

Pro Gln Pro Pro Ala Thr Leu Gln Ala Arg Asp Leu Pro Val Tyr Pro
        35                  40                  45

Ala Glu Leu Ser Leu Leu Asp Ser Thr Asp Pro Arg Ala Trp Leu Thr
    50                  55                  60

Pro Thr Leu Gln Gly Leu Cys Thr Ala Arg Ala Ala Gln Tyr Leu Leu
65                  70                  75                  80

His Ser Pro Glu Leu Gly Ala Ser Glu Ala Ala Pro Arg Asp Glu
                85                  90                  95

Ala Asp Ser Gln Gly Glu Leu Val Arg Arg Ser Gly Cys Gly Leu
            100                 105                 110

Ser Lys Ser Pro Gly Pro Val Lys Val Arg Glu Gln Leu Cys Lys Leu
        115                 120                 125

Lys Gly Gly Val Val Asp Glu Leu Gly Cys Ser Arg Gln Arg Ala
130                 135                 140

Pro Ser Ser Lys Gln Val Asn Gly Val Gln Lys Gln Arg Leu Ala
145                 150                 155                 160

Ala Asn Ala Arg Glu Arg Arg Met His Gly Leu Asn His Ala Phe
                165                 170                 175

Asp Gln Leu Arg Asn Val Ile Pro Ser Phe Asn Asn Asp Lys Lys Leu
            180                 185                 190

Ser Lys Tyr Glu Thr Leu Gln Met Ala Gln Ile Tyr Ile Asn Ala Leu
        195                 200                 205

Ser Glu Leu Leu Gln Thr Pro Asn Val Gly Glu Gln Pro Pro Pro
    210                 215                 220

Thr Ala Ser Cys Lys Asn Asp His His His Leu Arg Thr Ala Ser Ser
225                 230                 235                 240

Tyr Glu Gly Gly Ala Gly Ala Ser Ala Val Ala Gly Ala Gln Pro Ala
                245                 250                 255

Pro Gly Gly Gly Pro Arg Pro Thr Pro Pro Gly Pro Cys Arg Thr Arg
            260                 265                 270

Phe Ser Gly Pro Ala Ser Ser Gly Gly Tyr Ser Val Gln Leu Asp Ala
        275                 280                 285

Leu His Phe Pro Ala Phe Glu Asp Arg Ala Leu Thr Ala Met Met Ala
    290                 295                 300

Gln Lys Asp Leu Ser Pro Ser Leu Pro Gly Gly Ile Leu Gln Pro Val
305                 310                 315                 320

Gln Glu Asp Asn Ser Lys Thr Ser Pro Arg Ser His Arg Ser Asp Gly
                325                 330                 335

Glu Phe Ser Pro His Ser His Tyr Ser Asp Ser Asp Glu Ala Ser
            340                 345                 350

<210> SEQ ID NO 19
<211> LENGTH: 351
<212> TYPE: PRT
<213> ORGANISM: Mus musculus

```
<400> SEQUENCE: 19

Met Ser Arg Leu Leu His Ala Glu Glu Trp Ala Glu Val Lys Glu Leu
1               5                   10                  15

Gly Asp His His Arg His Pro Gln Pro His His Val Pro Pro Leu Thr
            20                  25                  30

Pro Gln Pro Ala Thr Leu Gln Ala Arg Asp Leu Pro Val Tyr Pro
        35                  40                  45

Ala Glu Leu Ser Leu Leu Asp Ser Thr Asp Pro Arg Ala Trp Leu Thr
    50                  55                  60

Pro Thr Leu Gln Gly Leu Cys Thr Ala Arg Ala Ala Gln Tyr Leu Leu
65                  70                  75                  80

His Ser Pro Glu Leu Gly Ala Ser Glu Ala Ala Pro Arg Asp Glu
                85                  90                  95

Ala Asp Ser Gln Gly Glu Leu Val Arg Arg Ser Gly Cys Gly Gly Leu
            100                 105                 110

Ser Lys Ser Pro Gly Pro Val Lys Val Arg Glu Gln Leu Cys Lys Leu
        115                 120                 125

Lys Gly Gly Val Val Asp Glu Leu Gly Cys Ser Arg Gln Arg Ala
130                 135                 140

Pro Ser Ser Lys Gln Val Asn Gly Val Gln Lys Gln Arg Leu Ala
145                 150                 155                 160

Ala Asn Ala Arg Glu Arg Arg Met His Gly Leu Asn His Ala Phe
                165                 170                 175

Asp Gln Leu Arg Asn Val Ile Pro Ser Phe Asn Asn Asp Lys Lys Leu
            180                 185                 190

Ser Lys Tyr Glu Thr Leu Gln Met Ala Gln Ile Tyr Ile Asn Ala Leu
        195                 200                 205

Ser Glu Leu Leu Gln Thr Pro Asn Val Gly Glu Gln Pro Pro Pro
210                 215                 220

Thr Ala Ser Cys Lys Asn Asp His His Leu Arg Thr Ala Ser Ser
225                 230                 235                 240

Tyr Glu Gly Gly Ala Gly Ala Ser Ala Val Ala Gly Ala Gln Pro Ala
                245                 250                 255

Pro Gly Gly Gly Pro Arg Pro Thr Pro Pro Gly Pro Cys Arg Thr Arg
            260                 265                 270

Phe Ser Gly Pro Ala Ser Ser Gly Gly Tyr Ser Val Gln Leu Asp Ala
        275                 280                 285

Leu His Phe Pro Ala Phe Glu Asp Arg Ala Leu Thr Ala Met Met Ala
    290                 295                 300

Gln Lys Asp Leu Ser Pro Ser Leu Pro Gly Gly Ile Leu Gln Pro Val
305                 310                 315                 320

Gln Glu Asp Asn Ser Lys Thr Ser Pro Arg Ser His Arg Ser Asp Gly
                325                 330                 335

Glu Phe Ser Pro His Ser His Tyr Ser Asp Ser Asp Glu Ala Ser
            340                 345                 350

<210> SEQ ID NO 20
<211> LENGTH: 354
<212> TYPE: PRT
<213> ORGANISM: Homo sapiens

<400> SEQUENCE: 20

Met Ser Arg Leu Leu His Ala Glu Glu Trp Ala Glu Val Lys Glu Leu
1               5                   10                  15
```

```
Gly Asp His His Arg Gln Pro Gln Pro His His Leu Pro Gln Pro Pro
             20                  25                  30

Pro Pro Pro Gln Pro Pro Ala Thr Leu Gln Ala Arg Glu His Pro Val
         35                  40                  45

Tyr Pro Pro Glu Leu Ser Leu Leu Asp Ser Thr Asp Pro Arg Ala Trp
 50                  55                  60

Leu Ala Pro Thr Leu Gln Gly Ile Cys Thr Ala Arg Ala Ala Gln Tyr
 65                  70                  75                  80

Leu Leu His Ser Pro Glu Leu Gly Ala Ser Glu Ala Ala Ala Pro Arg
                 85                  90                  95

Asp Glu Val Asp Gly Arg Gly Glu Leu Val Arg Arg Ser Ser Gly Gly
            100                 105                 110

Ala Ser Ser Ser Lys Ser Pro Gly Pro Val Lys Val Arg Glu Gln Leu
            115                 120                 125

Cys Lys Leu Lys Gly Gly Val Val Asp Glu Leu Gly Cys Ser Arg
        130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Met His Gly Leu Asn
                165                 170                 175

His Ala Phe Asp Gln Leu Arg Asn Val Ile Pro Ser Phe Asn Asn Asp
            180                 185                 190

Lys Lys Leu Ser Lys Tyr Glu Thr Leu Gln Met Ala Gln Ile Tyr Ile
            195                 200                 205

Asn Ala Leu Ser Glu Leu Leu Gln Thr Pro Ser Gly Gly Glu Gln Pro
210                 215                 220

Pro Pro Pro Pro Ala Ser Cys Lys Ser Asp His His Leu Arg Thr
225                 230                 235                 240

Ala Ala Ser Tyr Glu Gly Gly Ala Gly Asn Ala Thr Ala Ala Gly Ala
                245                 250                 255

Gln Gln Ala Ser Gly Gly Ser Gln Arg Pro Thr Pro Pro Gly Ser Cys
            260                 265                 270

Arg Thr Arg Phe Ser Ala Pro Ala Ser Ala Gly Gly Tyr Ser Val Gln
        275                 280                 285

Leu Asp Ala Leu His Phe Ser Thr Phe Glu Asp Ser Ala Leu Thr Ala
290                 295                 300

Met Met Ala Gln Lys Asn Leu Ser Pro Ser Leu Pro Gly Ser Ile Leu
305                 310                 315                 320

Gln Pro Val Gln Glu Glu Asn Ser Lys Thr Ser Pro Arg Ser His Arg
                325                 330                 335

Ser Asp Gly Glu Phe Ser Pro His Ser His Tyr Ser Asp Ser Asp Glu
            340                 345                 350

Ala Ser
```

<210> SEQ ID NO 21
<211> LENGTH: 354
<212> TYPE: PRT
<213> ORGANISM: Homo sapiens

<400> SEQUENCE: 21

```
Met Ser Arg Leu Leu His Ala Glu Glu Trp Ala Glu Val Lys Glu Leu
1               5                  10                  15

Gly Asp His His Arg Gln Pro Gln Pro His His Leu Pro Gln Pro Pro
             20                  25                  30
```

```
Pro Pro Pro Gln Pro Pro Ala Thr Leu Gln Ala Arg Glu His Pro Val
            35                  40                  45

Tyr Pro Pro Glu Leu Ser Leu Leu Asp Ser Thr Asp Pro Arg Ala Trp
 50                  55                  60

Leu Ala Pro Thr Leu Gln Gly Ile Cys Thr Arg Ala Ala Gln Tyr
 65                  70                  75                  80

Leu Leu His Ser Pro Glu Leu Gly Ala Ser Glu Ala Ala Pro Arg
                85                  90                  95

Asp Glu Val Asp Gly Arg Gly Glu Leu Val Arg Ser Ser Gly Gly
            100                 105                 110

Ala Ser Ser Lys Ser Pro Gly Pro Val Lys Val Arg Glu Gln Leu
            115                 120                 125

Cys Lys Leu Lys Gly Val Val Asp Glu Leu Gly Cys Ser Arg
130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Met His Gly Leu Asn
                165                 170                 175

His Ala Phe Asp Gln Leu Arg Asn Val Ile Pro Ser Phe Asn Asn Asp
                180                 185                 190

Lys Lys Leu Ser Lys Tyr Glu Thr Leu Gln Met Ala Gln Ile Tyr Ile
                195                 200                 205

Asn Ala Leu Ser Glu Leu Leu Gln Thr Pro Ser Gly Gly Glu Gln Pro
            210                 215                 220

Pro Pro Pro Pro Ala Ser Cys Lys Ser Asp His His Leu Arg Thr
225                 230                 235                 240

Ala Ala Ser Tyr Glu Gly Gly Ala Gly Asn Ala Thr Ala Ala Gly Ala
                245                 250                 255

Gln Gln Ala Ser Gly Gly Ser Gln Arg Pro Thr Pro Gly Ser Cys
            260                 265                 270

Arg Thr Arg Phe Ser Ala Pro Ala Ser Ala Gly Gly Tyr Ser Val Gln
                275                 280                 285

Leu Asp Ala Leu His Phe Ser Thr Phe Glu Asp Ser Ala Leu Thr Ala
290                 295                 300

Met Met Ala Gln Lys Asn Leu Ser Pro Ser Leu Pro Gly Ser Ile Leu
305                 310                 315                 320

Gln Pro Val Gln Glu Glu Asn Ser Lys Thr Ser Pro Arg Ser His Arg
            325                 330                 335

Ser Asp Gly Glu Phe Ser Pro His Ser His Tyr Ser Asp Ser Asp Glu
                340                 345                 350

Ala Ser

<210> SEQ ID NO 22
<211> LENGTH: 356
<212> TYPE: PRT
<213> ORGANISM: Homo sapiens

<400> SEQUENCE: 22

Met Gln Ile Leu Ser Arg Cys Gln Gly Leu Met Ser Glu Glu Cys Gly
 1               5                  10                  15

Arg Thr Thr Ala Leu Ala Ala Gly Arg Thr Arg Lys Gly Ala Gly Glu
                20                  25                  30

Glu Gly Leu Val Ser Pro Glu Gly Ala Gly Asp Glu Asp Ser Cys Ser
            35                  40                  45
```

```
Ser Ser Ala Pro Leu Ser Pro Ser Ser Pro Arg Ser Met Ala Ser
    50              55                  60

Gly Ser Gly Cys Pro Pro Gly Lys Cys Val Cys Asn Ser Cys Gly Leu
65              70                  75                  80

Glu Ile Val Asp Lys Tyr Leu Lys Val Asn Asp Leu Cys Trp His
                85                  90                  95

Val Arg Cys Leu Ser Cys Ser Val Cys Arg Thr Ser Leu Gly Arg His
            100                 105                 110

Thr Ser Cys Tyr Ile Lys Asp Lys Asp Ile Phe Cys Lys Leu Asp Tyr
            115                 120                 125

Phe Arg Arg Tyr Gly Thr Arg Cys Ser Arg Cys Gly Arg His Ile His
    130                 135                 140

Ser Thr Asp Trp Val Arg Arg Ala Lys Gly Asn Val Tyr His Leu Ala
145                 150                 155                 160

Cys Phe Ala Cys Phe Ser Cys Lys Arg Gln Leu Ser Thr Gly Glu Glu
                165                 170                 175

Phe Ala Leu Val Glu Glu Lys Val Leu Cys Arg Val His Tyr Asp Cys
            180                 185                 190

Met Leu Asp Asn Leu Lys Arg Glu Val Glu Asn Gly Asn Gly Ile Ser
            195                 200                 205

Val Glu Gly Ala Leu Leu Thr Glu Gln Asp Val Asn His Pro Lys Pro
210                 215                 220

Ala Lys Arg Ala Arg Thr Ser Phe Thr Ala Asp Gln Leu Gln Val Met
225                 230                 235                 240

Gln Ala Gln Phe Ala Gln Asp Asn Asn Pro Asp Ala Gln Thr Leu Gln
                245                 250                 255

Lys Leu Ala Glu Arg Thr Gly Leu Ser Arg Arg Val Ile Gln Val Trp
            260                 265                 270

Phe Gln Asn Cys Arg Ala Arg His Lys Lys His Val Ser Pro Asn His
    275                 280                 285

Ser Ser Ser Thr Pro Val Thr Ala Val Pro Pro Ser Arg Leu Ser Pro
        290                 295                 300

Pro Met Leu Glu Glu Met Ala Tyr Ser Ala Tyr Val Pro Gln Asp Gly
305                 310                 315                 320

Thr Met Leu Thr Ala Leu His Ser Tyr Met Asp Ala His Ser Pro Thr
                325                 330                 335

Thr Leu Gly Leu Gln Pro Leu Leu Pro His Ser Met Thr Gln Leu Pro
            340                 345                 350

Ile Ser His Thr
        355

<210> SEQ ID NO 23
<211> LENGTH: 365
<212> TYPE: PRT
<213> ORGANISM: Mus musculus

<400> SEQUENCE: 23

Met Tyr Trp Lys Ser Asp Gln Met Phe Val Cys Lys Leu Glu Gly Lys
1               5                   10                  15

Glu Met Pro Glu Leu Ala Val Pro Arg Glu Met Cys Pro Gly Leu Met
            20                  25                  30

Ser Glu Glu Cys Gly Arg Pro Ala Ala Gly Ala Gly Arg Thr Arg Lys
        35                  40                  45

Gly Ser Gly Glu Glu Gly Leu Val Asn Pro Glu Gly Ala Gly Asp Glu
    50                  55                  60
```

```
Asp Ser Cys Ser Ser Ser Gly Pro Leu Ser Pro Ser Ser Pro Gln
 65              70              75              80

Ser Met Ala Ser Gly Pro Met Cys Pro Pro Gly Lys Cys Val Cys Ser
             85              90              95

Ser Cys Gly Leu Glu Ile Val Asp Lys Tyr Leu Leu Lys Val Asn Asp
            100             105             110

Leu Cys Trp His Val Arg Cys Leu Ser Cys Ser Val Cys Arg Thr Ser
            115             120             125

Leu Gly Arg His Thr Ser Cys Tyr Ile Lys Asp Lys Asp Ile Phe Cys
130             135             140

Lys Leu Asp Tyr Phe Arg Arg Tyr Gly Thr Arg Cys Ser Arg Cys Gly
145             150             155             160

Arg His Ile His Ser Thr Asp Trp Val Arg Arg Ala Lys Gly Asn Val
                165             170             175

Tyr His Leu Ala Cys Phe Ala Cys Phe Ser Cys Lys Arg Gln Leu Ser
                180             185             190

Thr Gly Glu Glu Phe Ala Leu Val Glu Glu Lys Val Leu Cys Arg Val
            195             200             205

His Phe Asp Cys Met Leu Asp Asn Leu Lys Arg Glu Val Glu Asn Gly
            210             215             220

Asn Gly Ile Ser Val Glu Gly Ala Leu Leu Thr Glu Gln Asp Val Asn
225             230             235             240

His Pro Lys Pro Ala Lys Arg Ala Arg Thr Ser Phe Thr Ala Asp Gln
            245             250             255

Leu Gln Val Met Gln Ala Gln Phe Ala Gln Asp Asn Asn Pro Asp Ala
            260             265             270

Gln Thr Leu Gln Lys Leu Ala Glu Arg Thr Gly Leu Ser Arg Arg Val
            275             280             285

Ile Gln Val Trp Phe Gln Asn Cys Arg Ala Arg His Lys Lys His Val
    290             295             300

Ser Pro Asn His Ser Ser Ser Ala Pro Val Thr Ala Val Pro Ser Ser
305             310             315             320

Arg Leu Ser Pro Pro Ile Leu Glu Glu Met Ala Tyr Ser Ala Tyr Asp
                325             330             335

Pro Gln Asp Asp Gly Met Leu Thr Ala His Ser Tyr Leu Asp Ala His
            340             345             350

Gln Gln Leu Leu Asp Ser Ser Pro Cys Tyr Pro Ile Gln
            355             360             365
```

METHODS AND PRODUCTS FOR BIASING CELLULAR DEVELOPMENT

CROSS-REFERENCE TO RELATED APPLICATIONS

This application claims priority to U.S. Ser. No. 60/621,483 filed Oct. 22, 2004; and is a divisional application of U.S. application Ser. No. 13/330,957, filed Dec. 20, 2011, which is a divisional application of U.S. application Ser. No. 11/258,603, filed Oct. 24, 2005, which hereby incorporated in their entirety.

FIELD OF INVENTION

The present invention is directed to methods and systems directed to altering the differentiation of a cell, more particularly to biasing a multipotent stem cell by transfecting the cell with a nucleic acid sequence comprising a desired gene, the gene being expressed so that the cell, or its progeny, differentiate to a desired end-stage cell.

BACKGROUND

Proper cellular function and differentiation depends on intrinsic signals and extracellular environmental cues. These signals and cues vary over time and location in a developing organism (i.e., during embryogenesis), and remain important in developing and differentiating cells during post-natal growth and in a mature adult organism. Thus, in a general sense, the interplay of the dynamically changing set of intracellular dynamics (such as manifested by intrinsic chemical signaling and control of gene expression) and environmental influences (such as signals from adjacent cells) determine cellular activity. The cellular activity so determined is known to include cell migration, cell differentiation, and the manner a cell interacts with surrounding cells.

The use of stem cells and stem-cell-like cells of various types for cell replacement therapies, and for other cell-introduction-based therapies, is being actively pursued by a number of researchers. Embryonic stems cells from a blastocyst stage are frequently touted for their pluripotency—that is, their ability to differentiate into all cell types of the developing organism. Later-stage embryonic stem cells, and certain cells from generative areas of an adult organism, are identified as more specialized, multipotent stem cells. These cells include cells that are able to give rise to a succession of a more limited subset of mature end-stage differentiated cells of particular types or categories, such as hematopoietic, mesenchymal, or neuroectodermal end-stage differentiated cells. For example, a multipotent neural stem cell may give rise to one or more neuron cell types (i.e., cholinergic neuron, dopaminergic neuron, GABAergic neurons), which includes their specific cell classes (i.e., a basket cell or a chandelier cell for GABAergic neurons), and to non-neuron glial cells, such as astrocytes and dendrocytes.

Further along the path of differentiation are cells derived from multipotent stem cells. For example, derivatives of a localized, non-migrating neuroectodermal type stem cell may migrate but, compared to their multipotent parent, have more limited abilities to self-renew and to differentiate (See Stem Cell Biology, Marshak, Gardner & Gottlieb, Cold Spring Harbor Laboratory Press, 2001, particularly Chapter 18, p. 407). Some of these cells are referred to a neuron-restricted precursors ("NRPs"), based on their ability, under appropriate conditions, to differentiate into neurons. There is evidence that these NRPs have different subclasses, although this may reflect different characteristics of localized multipotent stem cells (Stem Cell Biology, Marshak et al., pp 418-419).

One advantage of use of mulitpotent and more committed cells further along in differentiation, compared to pluripotent embryonic stem cells, is the reduced possibility that some cells introduced into an organism from such source will form a tumor (Stem Cell Biology, Marshak et al., p. 407). However, a disadvantage of cells such as cell types developed from multipotent stem cells, for instance, embryonic progenitor cells, is that they are not amenable to ongoing cell culture. For instance, embryonic neural progenitor cells, which are able to differentiate into neurons and astrocytes, are reported to survive only one to two months in a cell culture.

Generally, it is known in the art that the lack of certain factors critical to differentiation will result in no or improper differentiation of a stem cell. Researchers also have demonstrated that certain factors may be added to a culture system comprising stem cells, such as embryonic stem cells, so that differentiation to a desired, stable end-stage differentiated cell proceeds. It also is known in the art to introduce and express a transcription factor gene, Nurr1, into embryonic stem cells, and then process the cells through a five-step differentiation method (Kim, Jong-Hoon et al., Dopamine Neurons Derived from Embryonic Stem Cells Function in an Animal Model of Parkinson's Disease, Nature, 418:50-56 (2002)), resulting in differentiated cells having features of dopaminergic cells. However, the starting cell for this was an embryonic stem cell, and the differentiation process through to a cell having the features of a dopaminergic neuron, requires substantial effort that includes the addition and control of endogenous factors. In addition, because the starting cell is an early-stage embryonic stem cell having pluripotency, there is a relatively higher risk that some cells implanted from this source will become tumerogenic.

Also, without being bound to a particular theory, it is believed that to the extent a particular method of differentiation results in a greater percentage of cells that are dedicated or predetermined to differentiate to a desired functional cell type (i.e., a cholinergic neuron), this reduces the chance of tumor formation after introduction of cells derived from such method. As disclosed herein, embodiments of the present method that utilize multipotent stem cells as the starting material provide an increased percentage of cells predisposed (i.e., biased) to or differentiated to a desired cell type. This is believed to provide for reduced risk of tumor formation equivalent to or superior to the use of more differentiated cells such as NRPs.

There are many possible applications for methods, compositions, and systems that provide for improved differentiation of stem cells to a desired functional, differentiated cell. For example, not to be limiting, millions of people suffer from deafness and balance defects caused by damage to inner ear hair cells (IEHCs), the primary sensory receptor cells for the auditory and vestibular system after exposure to loud noises, antibiotics, or antitumor drugs. Since IEHCs rarely regenerate in mammals, any damage to these organs is almost irreversible, precludes any recovery from hearing loss, and results in potentially devastating consequences. Current therapies utilizing artificial cochlear implants or hearing aids may partially improve but not sufficiently restore hearing. Therefore, cell therapy to replace the damaged IEHC may be one of the most promising venues today. In the past, IEHC production from progenitor cells from the vestibular sensory epithelium of the bullfrog {Cristobal, 1998 #28} and possible existence of IEHC progenitors in mammalian cochlea sensory epithelia {Kojima, 2004 #29} has been reported. However limited quantity of IEHC progenitor prevents clinical application of this type of cell to treat deafness. Thus novel technology to produce IEHCs from other cell sources is needed.

While stem cells are known to be the building blocks responsible for producing all of a body's cells, the specific differentiation process towards to IEHC linage is not clear. Embryonic stem cells transplanted into the inner ear of adult mice or embryonic chickens did not differentiate into IEHCs {Sakamoto, 2004 #19}. Neural stem cells (NSCs) grafted into the modiolus of cisplatin-treated cochleae of mice only differentiated into glial or neuronal cells within the cochleae {Tamura, 2004 #18}. In order to produce IEHCs from these stem cells, modification or direction of the cell fate decision may be needed.

Another possible application for methods, compositions, and systems of the present invention is biasing Human Neural Stem Cells ("HNSCs") to differentiate to cholinergic neurons, or to cells having characteristics of cholinergic neurons. Such biasing would provide for an improved percentage of such stem cells in a culture vessel to differentiate to this desired end-stage nerve cell. Improvements to the percentage of cells that are known to be biased to differentiate to this end-stage neuron cell, or to cells having characteristics of a cholinergic neuron, may lead to improvements both in research and treatment technologies for diseases and conditions that involve degeneration or loss of function of cholinergic neurons. Alzheimer's disease is one example of a malady known to be associated with degeneration of the long-projecting axons of cholinergic neurons.

Thus, there is a need in the art to improve the compositions, methods and systems that provide biased and/or differentiated cells from stem cells or stem-cell-like cells. More particularly, a need exists to obtain a higher percentage of desired cells from a pre-implantation cell culture, such as starting from multipotent stem cells and obtaining a higher percentage of cells committed to differentiate to a specified type of functional nerve cell, such as cholinergic neurons or inner ear hair cells. The present invention addresses these needs.

BRIEF DESCRIPTION OF THE FIGURES

FIG. 1 A Hath1 gene (SEQ ID NO:4) was amplified from the *homo sapiens* BAC clone RP11-680J17 by PCR and then cloned it into a mammalian expression directional cloning vector, pcDNAHismax TOPO TA.

FIG. 2 the hair cell marker calretinin was identified on certain cells via immunocytochemistry.

FIG. 3 Math 1 full length MRNA was amplified by RT-PCR and digested with Apai, which cuts position 441 of Hath1ORF. Expecting fragment sizes are 441 by and 624 bp. M: 100 bp marker; 5, 6, without transfection (control); 7, 8: transfected with mammalian expression vector containing Hath2.

FIG. 4 The presence of the actual protein calretinin on the cell surface was determined via Western Blot. Seven days for differentiation was allowed before any analysis of the cells. Protein was isolated from the cells and calretinin was identified in the cell isolate.

FIG. 5 Cells transfected with Hath1 and grown to allow for differentiation were visualized using Transmission Electron Microscopy. A subset of the cells exhibited distinct hair-like projections. These were the actual hairs from the transfected HNSCs that differentiated into cells having this characteristic feature of IEHCs.

FIG. 6 is another view of hair-like projections as shown in FIG. 5.

FIG. 7 LA-N-2 cells treated with RA expressed Lhx8, βIII-tubulin, and ChAT. FIG. 7A shows LA-N-2 cells stained red indicating the presence of βIII-tubulin. FIG. 7B shows LA-N-2 cells stained green indicating the presence of ChAT. FIG. 7C shows LA-N-2 cells stained green indicating the presence of NGF (blue stain indicating counter-staining for nuclei by DAPI). FIG. 7D (insert) shows non-specific staining for ChAT.

FIG. 8. The Gbx1 cDNA sequence (SEQ ID NO: 9) is inserted into the enhanced green flouroscent protein (EGFP) vector pEGFP-C1 ((BDBiosciences Clontech) at the EcoRI site within the vector's multiple cloning site, which is 3' of a CMV promoter and the EGFP gene.

FIG. 9: Phase contrast micrographs of LA-N2 cells. FIG. 9a: LA-N2 cells grow in clusters as adherent fibroblasts-like cells, occasionally cells extend short processes and form neuronal-like networks. FIG. 9b: LA-N2 cells treated with 10-6 μM retinoic acid.

FIG. 10: Lhx8 expression in the LA-N-2 and HNSCs cells. FIG. 10a: Shows gene expression with RT-PCR analysis of LA-N-2 cells treated with ten μM RA showed an increased expression of Lhx8 (394 bp) and ChAT (splice variants ~600 and 400 bp, respectively, compared with non-treated cells. FIG. 10b: represents RT-PCR analysis of Lhx8 expression in HNSCs 48 hours post-transfection.

FIG. 11: In vitro differentiation of Lhx8-transfected HNSCs. HNXCs tranfected with Lhx8 (a) in co-culture with LA-N-2 cellls and serum-free conditions differentiated mostly neurons with long extended processes after 10-14 days (b-f).

FIG. 12: Differentiated HNSCs/Lhx8 in co-culture with LA-N-2 cells. Cells were double-immunofluorescence stained with (a) βIII-tubulin (red) and (b) ChAT (green), markers for colinergic neurons (c) two localization of βIII-tubulin and ChAT. Blue signal is a counter staining for nuclei by DAPI.

FIG. 13: Differentiated HNSCs/LHX8 in co-culture with law and 2 cells. Cells were double immunofluorescence stained with (a) βIII-tubulin (green) and (b) CHAT (red), markers for colinergic neurons (c) co-localization of βIII-tubulin and CHAT. (20× magnification) blue signal is a counter staining for nuclei for DAPI. (d) insert for non0-specific staining for c βIII-tubulin and CHAT, respectively.

FIG. 14 Differentiated HNSCs/Lhx8 in co-culture with LA-N-2 cells. A) βIII-tubulin (green) and b) ChAT (red), markers for cholinergic neurons, c) co-localization of βIII-tubulin & ChAT. Blue signal is a counter staining for nuclei by DAPI (40× magnification).

FIG. 15 Differentiated non-transfected HNSCs in co-culture with LA-N-2 cells. Cells were double-immunofluorescence stained with βIII-tubulin (green) and nuclei counter staining by DAPI (Blue). No Chat-positive neurons were observed. (a-b) 10× and (c) 20× magnification, respectively.

FIG. 16 Differentiated non-transfected HNSCs in co-culture with LA-N-2 cells. Cells were double-immunofluorescense stained with (a-b) βIII-tubulin (green) and (c) GFAP (red) markers for neurons and astrocytes, respectively. Blue signal is a counter staining for nuclei by DAPI.

DETAILED DESCRIPTION OF EMBODIMENTS OF THE INVENTION

Figure 1:
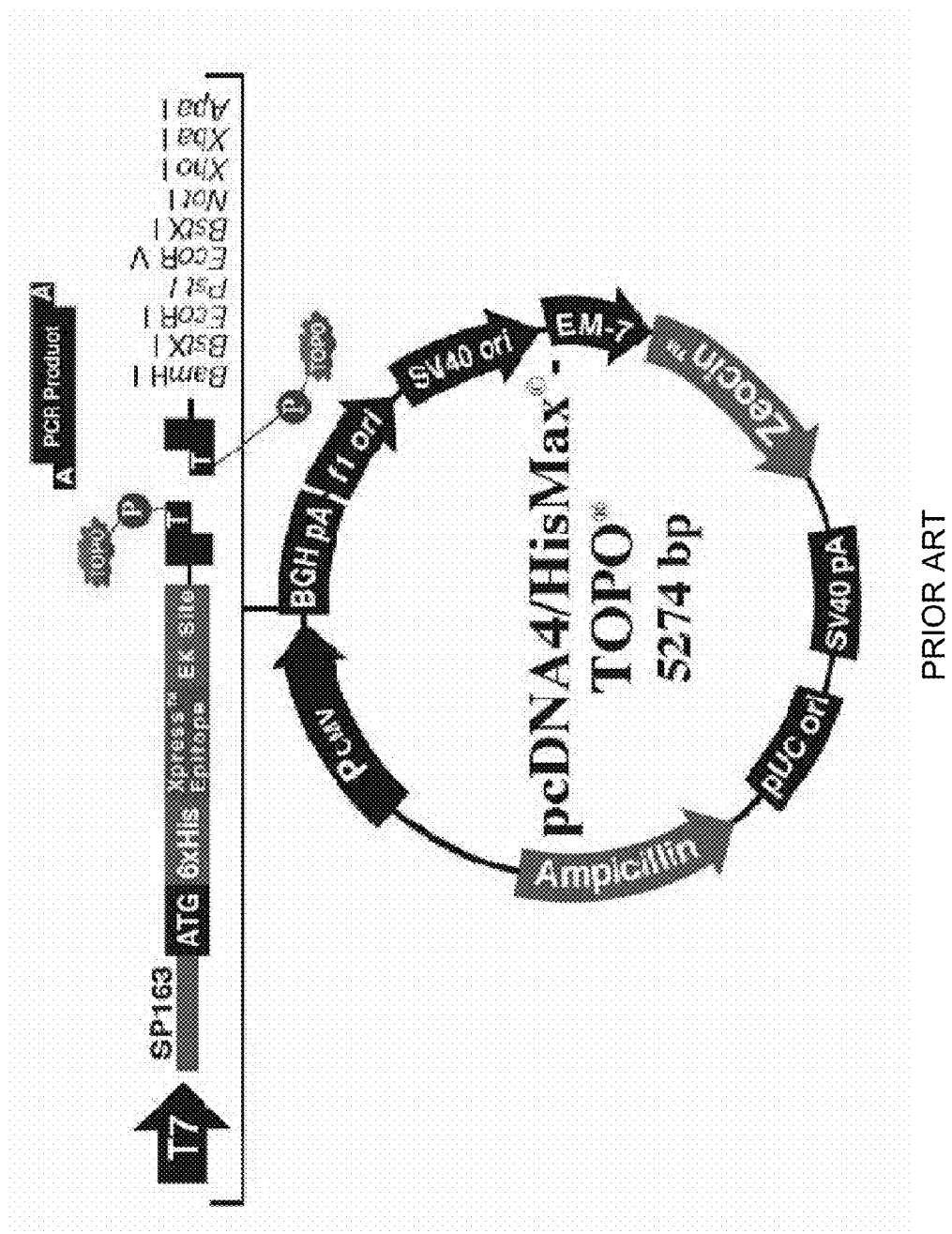
FIGS. 1-16 are appended hereto, are part of the specification, and are described herein and/or on the figures themselves.

In reviewing the detailed disclosure which follows, and the specification more generally, it should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

DEFINITIONS

Stem cells are undifferentiated cells that exist in many tissues of embryos and adult organisms. In embryos, blastocyst stem cells are the source of cells that differentiate to form the specialized tissues and organs of the developing fetus. In adults, specialized stem cells in individual tissues are the source of new cells, replacing cells lost through cell death due to natural attrition, disease, or injury. Stem cells may be used as substrates for producing healthy tissue where a disease, disorder, or abnormal physical state has destroyed or damaged normal tissue.

Five defining characteristics of stem cells have been advanced (from Weiss et al., 1996). That is, stems cells generally are recognized as having the ability to:
1. Proliferate: Stem cells are capable of dividing to produce daughter cells.
2. Exhibit self-maintenance or renewal over the lifetime of the organism: Stem cells are capable of reproducing by dividing symmetrically or asymmetrically to produce new stem cells. Symmetric division occurs when one stem cell divides into two daughter stem cells. Asymmetric division occurs when one stem cell forms one new stem cell and one progenitor cell. Symmetric division is a source of renewal of stem cells. This permits stem cells to maintain a consistent level of stem cells in an embryo or adult mammal.
3. Generate large number of progeny: Stem cells may produce a large number of progeny through the transient amplification of a population of progenitor cells.
4. Retain their multilineage potential over time: The various lines of stem cells collectively are the ultimate source of differentiated tissue cells, so they retain their ability to produce multiple types of progenitor cells, which in turn develop into specialized tissue cells.
5. Generate new cells in response to injury or disease: This is essential in tissues which have a high turnover rate or which are more likely to be subject to injury or disease, such as the epithelium or blood cells.

Thus, key features of stem cells include their capability of self-renewal, and their capability to differentiate into a range of end-stage differentiated tissue cells.

By "neural stem cell" (NSC) is meant a cell that (i) has the potential of differentiating into at least two cell types selected from a neuron, an astrocyte, and an oligodendrocyte, and (ii) exhibits self-renewal, meaning that at a cell division, at least one of the two daughter cells will also be a stem cell. Generally, the non-stem cell progeny of a single NSC are capable of differentiating into neurons, astrocytes, Schwann cells, and oligodendrocytes. Hence, a stem cell such as a neural stem cell is considered "multipotent" because its progeny have multiple differentiative pathways. Under certain conditions an NSC also may have the potential to differentiate as another non-neuronal cell type (e.g., a skin cell, a hematopoietic cell, a smooth muscle cell, a cardiac muscle cell, a skeletal muscle cell, a bone cell, a cartilage cell, a pancreatic cell or an adipocyte).

By "Human Neural Stem Cell" ("HNSC") is meant a neural stem cell of human origin. A HNSC may be of fetal origin, or adult origin from a neural source, or may be derived from other cell sources, such as by de-differentiating a cell of mesenchymal origin. As to the latter, for example see U.S. application serial number 2003/0219898, which is incorporated by reference, inter alia, specifically for this teaching. HNSCs of the invention are distinguished from natural HNSCs by their adaptation for proliferation, migration and differentiation in mammalian host tissue when introduced thereto.

By a "population of cells" is meant a collection of at least ten cells. A population may consist of at least twenty cells, or of at least one hundred cells, or of at least one thousand or even one million cells. Because the NSCs of the present invention exhibit a capacity for self-renewal, they can be expanded in culture to produce a collection of large numbers of cells.

By "potent cell" is meant a stem cell that has the capability to differentiate into a number of different types of end-stage cell types, and to self-renew, and may include stem cells classified as pluripotent, multipotent, or cells more differentiated than multipotent (i.e., a dedicated progenitor) under different stem cell classification schemes.

By "a presumptive end-stage cell" is meant a cell that has acquired characteristics of a desired end-stage cell type, but which has not been conclusively identified as being the desired end-stage cell. A presumptive end-stage cell possesses at least two, and often more, morphological and/or molecular phenotypic properties of the desired end-stage cell.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 3$^{rd}$ Ed., ed. by Sambrook, Fritsch and Maniatis (Cold Spring Harbor Laboratory Press: 2001); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

U.S. Patent Application Nos. 2003/0219898, 2003/0148513, and 2003/0139410 are incorporated by reference to the extent they are not inconsistent with the teachings herein. The first two of these patent applications describe multiple uses of increased potency cells obtained from the taught methods, and in particular, the implantation of stem cells for different therapeutic treatments of neurological trauma and degenerative conditions. The third patent application is directed to the use of certain compounds to stimulate proliferation and migration of stem cells. Those skilled in the art will readily appreciate that the cells of the present invention could be obtained, or their effectiveness enhanced, by combining with the teachings of the aforementioned patent applications, without undue experimentation.

The present invention is directed to compositions, methods and systems that provide for increased percentage of neural stem cells and other multipotent or potent stem cells to become committed, or predisposed, to differentiate to a desired end-stage differentiated nerve cell. More particularly, the present invention utilizes the introduction into such a stem cell of a nucleic acid sequence comprising a developmental control gene. A developmental control gene as used in the present invention may encode a transcription factor, cell-surface molecule, or a secreted signal molecule (See Fundamental Neuroscience, Zigmond, Bloom, Landis, Roberts and Squire, Academic Press, 1999, Chapter 15). Examples below provide details of the introduction of three transcription factor type genes—Lhx8 and Gbx1 that improve differentiation of human neural stem cells (HNSCs) to cells having characteristics of cholinergic neurons, and Hath1 that improves differentiation of HNSCs to cells having characteristics of inner ear hair cells (IEHCs). The effectiveness of these single-gene introductions to such cells is unexpected and surprising in view of the subtlety and complexity of differentiation of multipotent stem cells to cells such as neural cells like cholinergic nerve cells and inner ear hair cells. Other development control genes having capability to achieve similar desired results are disclosed.

The present invention advances the art by demonstrating the utility, in multipotent stem cells, of introducing for expression a nucleic acid sequence that comprises a desired developmental control gene. One example of such introducing is transfection by a vector comprising the nucleic acid sequence. After such introducing, the introduced developmental control gene is expressed in the cell (or its progeny), at least transiently. By so altering a multipotent stem cell, the present invention provides for more consistent differentiation to a desired functional cell type, such as a cholinergeric nerve cell. In doing so, this is believed to reduce known risks of this type of cell transplantation, such as the risk of tumor growth upon implantation of cells from pluripotent embryonic cell cultures.

Thus, in some embodiments the present invention is directed to biasing a multipotent cell such that the cell becomes programmed, or biased, to differentiate into a desired cell type under appropriate external conditions. This is done in some embodiments so that in a pre-implantation cell culture a greater percentage of cells are either pre-disposed to differentiate to and/or do differentiate to a desired cell type. More particularly, in certain embodiments of this biasing, the cell is transformed so it expresses a certain factor that biases the same cells to differentiate to a desired cell type upon a later implantation to a particular tissue in a living organism. In such embodiments, this improves a differentiation ratio so that a higher percentage of cells introduced into a particular cell medium, a tissue culture, or a living organism in a particular location differentiate into the end-stage differentiated cell type that is desired. Without being bound to a particular theory, this is believed to increase the probability of success and overall effectiveness, and to decrease the risks associated with implantation of cells obtained from embryonic stem cells or embryonic-cell-like cells.

While not meant to be limiting as to the type of nucleic acid sequence introduced, examples herein utilize introduction to a cell of a nucleic acid sequence comprising a homeobox gene. This is a gene group that includes a number of known developmental control genes. A homeobox gene is a gene containing an approximately 180-base-pair segment (the "homeobox") that encodes a protein domain involved in binding to (and thus regulating the expression of) DNA. The homeobox segment is remarkably similar in many genes with different functions. However, specific homeobox genes are known to operate at different stages, and in different tissue environments, to yield very different specific results. For example, in relatively early embryological development in the vertebrate embryo, expression of genes of the Hox family of homeobox genes appears to affect development of the brain based on position along the anterior/posterior axis. This is believed to control identity and phenotypic specializations of individual rhombomeres. (Fundamental Neuroscience, Zigmond et al., p. 435). Later in development, LIM homeobox gene expression is associated with the projection pattern of developing primary motor neurons, and more generally, expression of a particular combination of LIM homeobox genes appears to be related to motor neuron subtype identity and to targeting specificity (Fundamental Neuroscience, Zigmond et al., p. 507). Also, some LIM homeobox genes appear to affect developmental progression, rather than fate, of motor neurons, which suggests a role of cell-to-cell signaling in the embryo to fully effectuate the differentiation in vivo (Fundamental Neuroscience, Zigmond et al., pp. 443-444). These highly specialized and variable roles for homeobox genes in general, and for LIM family homeobox genes more particularly, demonstrate the subtle, specific, and highly variable effects that these genes may have on cell and tissue development and differentiation.

Further with regard to function of homeobox genes, these genes encode transcriptional regulators that play critical roles in a variety of developmental processes. Although the genetic and developmental mechanisms that control the formation of forebrain cholinergic neurons are just beginning to be elucidated, it is known that the vast majority of forebrain cholinergic neurons derive from a region of the subcortical telencephalon that expresses the Nkx2-1 homeobox gene.

It has recently been reported that Nkx2-1 appears to specify the development of the basal telencephalon by positively regulating transcription factors such as the LIM-homeobox genes Lhx8 (also known as L3 or Lhx7) and Gbx1, which are associated with the development of cholinergic neurons in the basal forebrain (Zhao et al., 2003; Asbreuk et al., 2002, Waters et al., 2003).

In the spinal cord, IsL1, Lhx1, Lhx3 and Lhx4 have been shown to be important for the development of spinal cord cholinergic neurons (Pfaff et al., 1996; Sharma et al., 1998; Kania et al., 2000). Given that the spinal cord cholinergic neurons are reported to require multiple LIM-homeobox genes for their development, it is expected that Lhx8 is not the only LIM-homeobox gene that is required in generating telencephalic cholinergic neurons. Other candidates are Lhx6 and IsL1, which are also expressed in the basal telencephalon (Marin et al., 2000). Also, it is suggested that Dlx1/2 and Mash, though not directly regulating Lhx8, participate in controlling the number of cholinergic neurons that are formed in the telencephalon (Marin et al., 2000).

Thus, at a minimum, developmental control genes that may be used in the present invention to transfect cells to bias those cells (or their progeny) to differentiate to a desired end-stage cell type, here that cell type being cholinergic neurons, include, but are not limited to Lhx8, Gbx1, Lhx6, IsL1, Dlx1/2 and Mash.

The Human Neural Stem Cells (HNSCs), such as discussed in the examples below, are obtained from cultures that were started from clones obtained from human fetal brain tissue. One lineage was obtained by isolating individual cells from neurospheres of a fetal brain tissue sample obtained from Cambrex, and ultimately identifying one multipotent stem cell for clonal propagation. A second lineage was obtained by isolating a desired multipotent cell from a 9-week old fetal brain (Christopher L. Brannen and Kiminobu Sugaya, Neuroreport 11, 1123-8 (2000)). The HNSCs so obtained were maintained in serum-free medium, and have been demonstrated to have the capability to differentiate into neurons and glial cells such as astrocytes and dendrocytes.

The following examples are provided to further disclose the genesis, operation, scope and uses of embodiments of the present invention. These examples are meant to be instructive, and illustrative, and not to be limiting as to the scope of invention as claimed herein. These examples are to be considered with the referred to drawings.

Example 1

This example demonstrates that transfection of a human neural stem cell with Hath1 results in the transfected cell (or its progeny) differentiating into a cell having markers of an inner ear hair cell (IEHC). Hath1 (in humans) and Math1 (in mice) are basic helix-loop-helix transcription factors (and homologs of the *Drosophila* gene atonal) that are expressed in inner ear sensory epithelia. Since embryonic Math1-null mice failed to generate cochlear and vestibular hair cells, it appears to be required for the generation of inner ear hair cells (Bermingham N A, Hassan B A, Price S D, Vollrath M A, Ben-Arie N, Eatock R A, Bellen H J, Lysakowski A, Zoghbi H Y. 1999. Math1: An essential gene for the generation of inner ear hair cells. Science 284 (June 11): 1837-1841). Fate determination of mammalian IEHC is generally completed by birth. However, overexpression of Math1 in postnatal rat cochlear explant cultures resulted in production of extra hair cells from columnar epithelial cells located outside the sensory epithelium, which normally give rise to inner sulcus cells. Math1 expression also facilitated conversion of postnatal utricular supporting cells into hair cells (Zheng, G L, Gao Wq. 2000. Overexpression of Hath1 induces robust production of extra hair cells in postnatal rat inner ears. *Nat Neuroscience* June; 3(6):580-6). In vivo, Math1 overexpression leads to the appearance of immature hair cells in the organ of Corti and new hair cells adjacent to the organ of Corti in the interdental cell, inner sulcus, and Hensen cell regions, indicating nonsensory cells in the mature cochlea retain the competence to generate new hair cells after over expression of Math1 (Kawamoto K, Ishimoto S, Minoda R, Brough D E, Raphael Y. 2003. Math1 gene transfer generates new cochlear hair cells in mature guinea pigs in vivo. J Neurosci June 1; 23(11):4395-400). Based on the above-summarized work, it was hypothesized that Hath1 may be necessary, and sufficient as a single introduced gene for expression in a multipotent neural stem cell, to positively affect differentiation to an IEHC, or to a cell having characteristics of an IEHC.

A Hath1 gene (SEQ ID NO:4) was amplified from the *homo sapiens* BAC clone RP11-680J17 by PCR and then cloned it into a mammalian expression directional cloning vector, pcDNAHismax TOPO TA (See FIG. 1; 6×His tag disclosed as SEQ ID NO: 16). Upon the insertion of the Hath1 gene expressible sequence into the directional cloning vector, the expressible sequence was operatively linked to the CMV promoter, and was also positioned upstream (with regard to reading) of a polyadenylation transcription termination site. The clone was confirmed by sequencing of the insert.

An established a non-serum HNSC culture system was utilized to investigate the differentiation of human neural stem cells (HNSCs) within a defined condition. (Christopher L. Brannen and Kiminobu Sugaya, Regeneration and Transplantation, 11:5, 1123-1128 (2000)). The serum-free supplemented growth medium consisted of HAMS-F12 (Gibco, BRL, Burlington, ON), antibiotic/antimycotic mixture (1:100, Gibco), B27 (1:50, Gibco), human recombinant FGF-2 and EGF (20 ng/ml each, R and D Systems, Minneapolis, Minn.), and heparin (5 ug/ml, Sigma, St. Louis, Mo.). Cells were maintained in 20 ml of this medium at 37° C. in a 5% $CO_2$ humidified incubation chamber.

The mammalian expression vector containing Hath1 gene was transfected into HNSCs by using the Neuroporter Kit (Gene Therapy Systems, Inc. San Diego, Calif.) and Hath 1 gene expression was confirmed by RT-PCR. These Hath1-transfected HNSCs were differentiated for 7 days by the depletion of mitotic factors (FGF-2, EGF) from the culture media. After the differentiation the cells were fixed for immunocytochemistry and Electron Microscopy.

The immunocytochemistry revealed the existence of cells expressing calretinin, a hair cell marker, which were immunoreactive in this culture. These calretinin immunopositive cells resembled morphology of IEHC. The calretinin expression in the culture was also confirmed by Western blot, which showed single band specific to calretinin molecular weight (29 kD). Further electron microscopy analysis of the cells also showed a typical IEHC morphology. These results indicate that HNSCs transfected with a vector comprising a Hath1 gene differentiate into IEHCs or into cells having characteristics of IEHCs. Comparisons with non-transfected controls using Western blot and room temperature PCR showed the presence of Hath1 protein and Hath1 mRNA in cells transfected with Hath1, but not in the controls.

Thus, embodiments of the present method provide for improved approaches to obtain IEHCs, or cell having characteristics of IEHCs, that are derived from HNSCs. Embodiments of the present invention provide a higher percentage of a population of cells biased, or disposed, to differentiate to IEHCs, or to cells having characteristics of IEHCs. The HNSCs utilized in this example are readily and continuously cultured in serum-free culture medium. Without being limited, in vitro and in vivo studies and trials using cells so obtained from HNSCs may include electrophysiological assessment of the cells and investigation of functional recovery after transplantation of the cells into the animal model of deafness. Positive findings in such pre-clinical studies may advance the art farther toward treatment of deafness via cell transplantation therapy using IEHCs produced from HNSCs.

Material and Methods

Hath 1 Transfection

The human Hath1 gene (SEQ ID NO:1) is amplified from the *Homo sapiens* BAC clone RP11-680J17 by PCR, using a forward primer (5'-TCCGATCCTGAGCGTCCGAGCCTT-3', SEQ ID NO: 14) and reverse primer (5'-GCTTCTGTCAC-CTTCCTAACTTGCC-3', SEQ ID NO: 15). The PCR amplification is conducted in 20 µl volumes containing the BAC clone (100 ng), 1× amplification buffer, 1 μM of each primer, dNTP Mix (250 μM), and Taq DNA Polymerase (2.5 U). The PCR condition is 95° C. (30"), 59° C. (30"), 72° C. (60") for 35 cycles, with an initial denaturation of 95° C. (5') and final elongation of 72° C. (15'). The PCR amplified fragment is cloned into a directional pcDNAHismax TOPO TA vector and the clone is confirmed by sequencing of the insert.

The gene expression of Hath1 is assessed by RT-PCR with the following condition: 95° C. (60"), 56° C. (60"), 72° C. (60") for 35 cycles, with an initial denaturation of 95° C. (5') and final elongation of 72° C. (15'). The Hath1 gene is transfected into Human Neural Stem Cells (HNSCs) using the Neuroporter Kit. The Neuroporter kit utilizes a lipid-based transfection system for the use with cultured primary neurons, neuronal cell lines, and glial cells. DNA and Neuroporter are used in a ratio of 10 μg DNA/75 μl Neuroporter, utilizing 37.5 μl per well in a 6-well plate and with total volumes of 1.5 mL growth media per well. 10 μg of DNA is added to DNA Diluent to make a total volume of 125 μl; this is incubated for 5' at room temperature. 75 μl of the Neuroporter Reagent is added to serum-free media to make a final volume of 125 μl. These solutions are incubated for 10 minutes to allow Neuroporter/DNA complexes to form, and then added directly to the HNSCs in a 6-well plate. One day later, the media is replaced with fresh growth media; one day later, this is replaced with differentiation media (Basal Medium Eagle) to induce spontaneous differentiation. The cells are cultured for 1-2 weeks in a basal differentiation medium containing Eagle's salts and L-glutamine, which is not supplemented with FGF-2 or EGF, and is serum-free.

RT-PCR

TRIzol reagent is used to extract RNA for RT-PCR and protein for a Western Blot. 6 μl of the template RNA is added to 1× Reaction Mix, 1 μM of each Hath1-specific primer, and 1 μl of the RT-Platinum® Taq Mix. The total volume of the solution is 20 μl. The RT-PCR condition is 94° C. (15"), 59° C. (30"), 72° C. (60") for 40 cycles, with an initial denaturation of 55° C. (30') and 94° C. (5').

Immunocytochemistry

The cells are fixed with 4% paraformaldehyde for 30' at room temperature, washed in phosphate-buffered saline (PBS, pH 7.2), then blocked with 3% normal goat serum in PBS containing 0.05% Triton-X100 for 1 hour. The cells are incubated with primary antibody calretinin overnight at 4° C., with a dilution factor of (1:2000) in PBS containing 0.05% Triton-X100.

Following PBST washing, the cells are incubated with secondary antibody biotinylated anti-rabbit made in goat in PBS containing 0.05% Triton-X100 (PBST), with a dilution factor of 1:200. This incubation takes 1 hour. The cells are washed with PBST, and incubated with ABC reagent for 1 hour. Following a PBS wash and staining wih DAB for 5-8', the cells are washed with PBS and distilled water, then stained with methyl green (5'). The cells are washed with water, ethanol, and xylene, coverslipped with permount, and ready for viewing with microscopy.

Western Blot

A Western Blot is performed to assay protein expression. The protein is extracted with TRIzol reagent. 15 μl of the protein is loaded with the size marker on a PVDF membrane and run at 200 V and 110 mA/gel for 50'. The transfer is run overnight at 15V, 170 0 mA at 4° C. The membrane is then washed with PBST 2×10' while rotating, and blocked with 3% milk for 60'. This is washed 2×10' with PBST and blocked with the primary antibody calretinin (1:500) overnight at 4° C. After washing 3×5' with PBST the membrane is incubated with the secondary antibody (1:2000) and shaken for 1 hour.

For detection, 7.5 mL of ECL solution is warmed to room temperature and 187.5 μl of solution B is added to solution A. 7.5 mL is added to the membrane at RT for 5'. The membrane is then placed in an x-ray film cassette and exposed as needed for chemilumescent detection.

Electron Microscopy

Cells were fixed with 3% glutaraldehyde with cacodyate buffer 0.1M, and dehydrated with a series of alcohols beginning with 50% up to 100% absolute ethanol followed by hexamethyldislazne (HMDS). The cultured cells were allowed to air-dry at room temperature. The specimens were attached to aluminum stubs using double sided carbon coated tape, sputter-coated with Platinum and palladium using the Cressington 208 HR High Resolution Coater. Samples were viewed with a Jeol 6320F Field Emission Microscope (high resolution images) and recorded with a digital camera. Samples were also viewed with the Hitachi Variable pressure microscope in V-P mode (variable pressure mode) and digitals were captured.

Results

A non-serum HNSC culture system was utilized (Christopher L. Brannen and Kiminobu Sugaya, Regeneration and Transplantation, 11:5, 1123-1128 (2000)). This culture system provides for the differentiation and expansion of HNSCs in vitro in the absence of serum. This system provides for the observation of differentiation of HNSCs within a defined condition. These HNSCs have been cultured in a medium consisting of DMEM/F12, antibiotic-antimycotic mixture (1:100), B-27 supplement (1:50), human recombinant FGF-2 and EGF (20 ng/ml each), and heparin (5 μg/ml). These cells have been maintained at 37° C. in a 5% CO2 humidified incubation chamber for more than 3 years in the lab. These cells are CD133—(a stem cell marker, which is known to be expressed in stem cells) positive, and GFAP- and βIII-tubulin-negative before differentiation. Upon differentiation, various differentiated cells typically express glial fibrillary acidic protein (GFAP), or βIII-tubulin, which are glial and neuronal markers, respectively.

Figure 2:
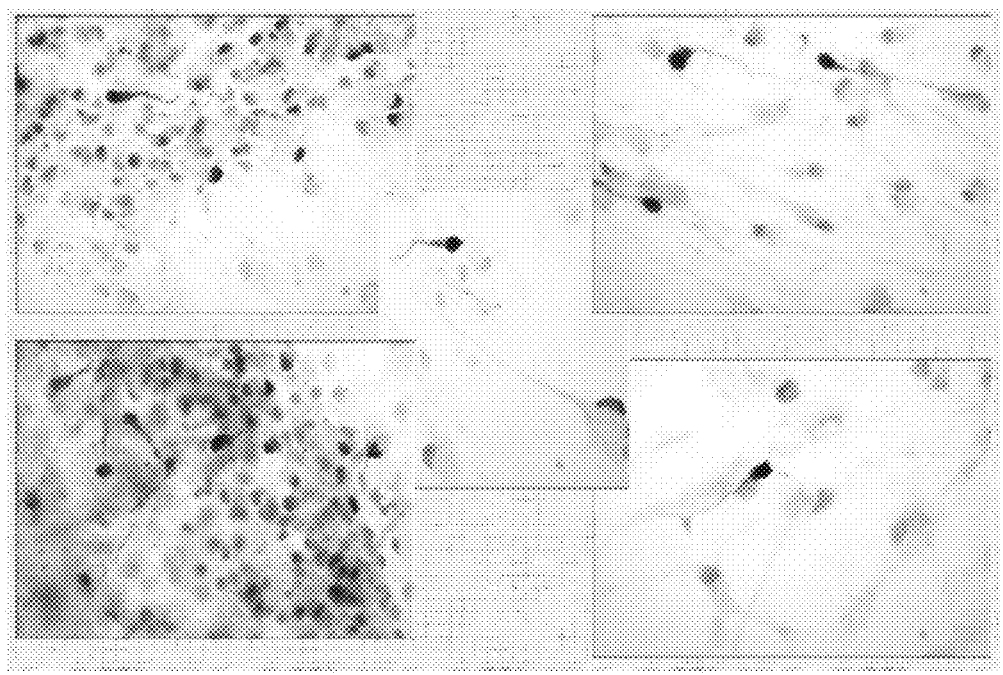
Figure 3:
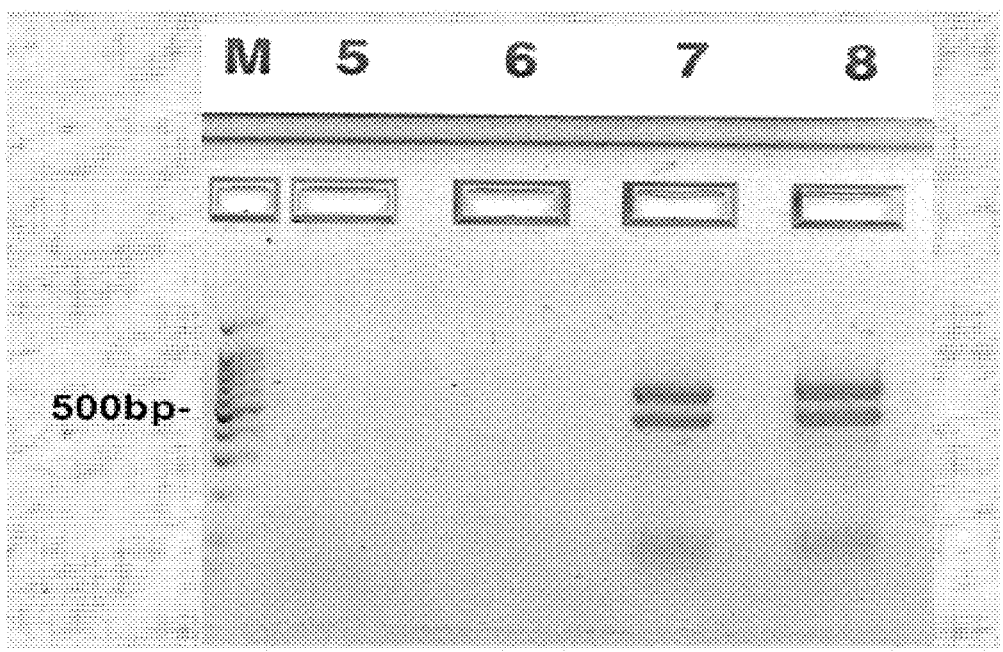

Preferential differentiation of HNSCs into IEHCs can be induced in vitro by the transfection of Hath1. The human Hath1 gene was amplified from the *Homo sapiens* BAC clone RP11-680J17 by PCR and cloned into a directional pcDNA-Hismax TOPO TA vector. This was confirmed by sequencing of the insert. After confirming expression of the gene by RT-PCR, the Neuroporter kit was utilized to tranfect HNSCs. These HNSCs were known to be viable and capable of differentiation, aggregating in neurospheres when multipotent. Once they began the process of differentiation, they left their neurospheres. After allowing 7 days for differentiation, these cells were either stained for hair cell specific markers or assayed for protein expression. Via immunocytochemistry, the hair cell marker calretinin was identified on certain cells (FIG. 2). Via RT-PCR, the expression of this protein was also verified (FIG. 3).

Figure 4:
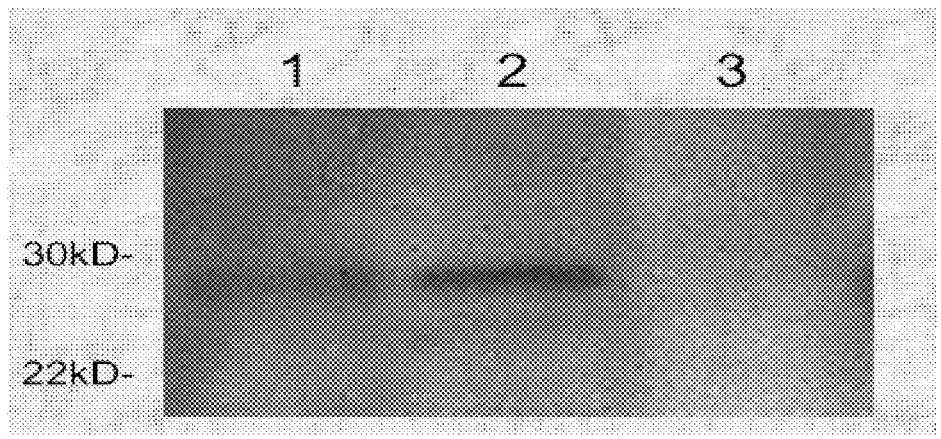

The presence of the actual protein calretinin on the cell surface was determined via Western Blot. Seven days for differentiation was allowed before any analysis of the cells. Protein was isolated from the cells and calretinin was identified in the cell isolate (FIG. 4).

Figure 5:
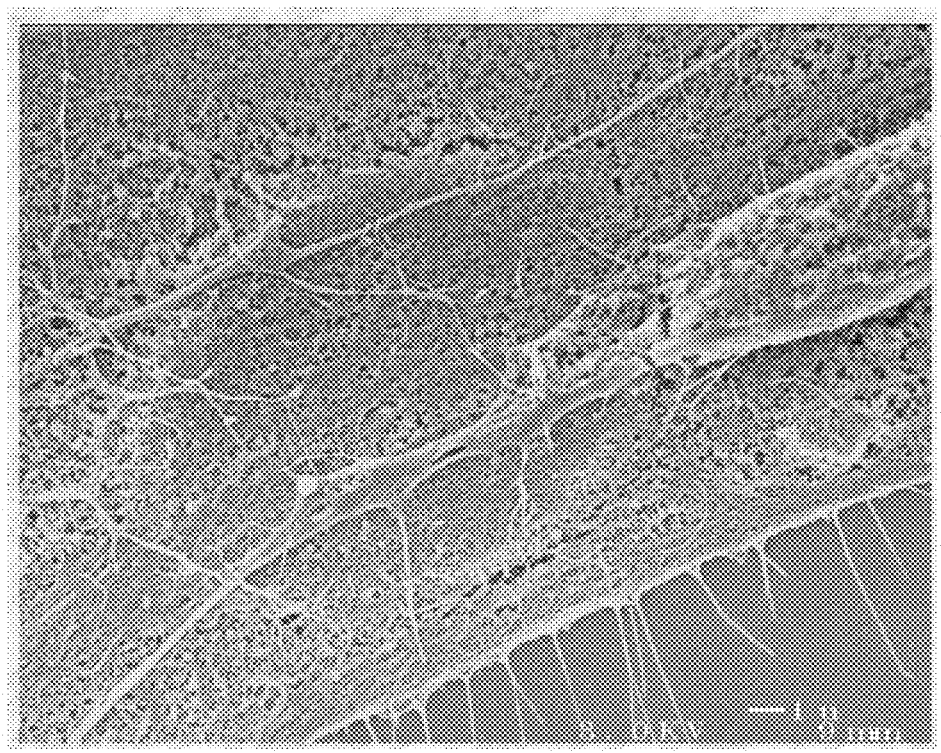
Figure 6:
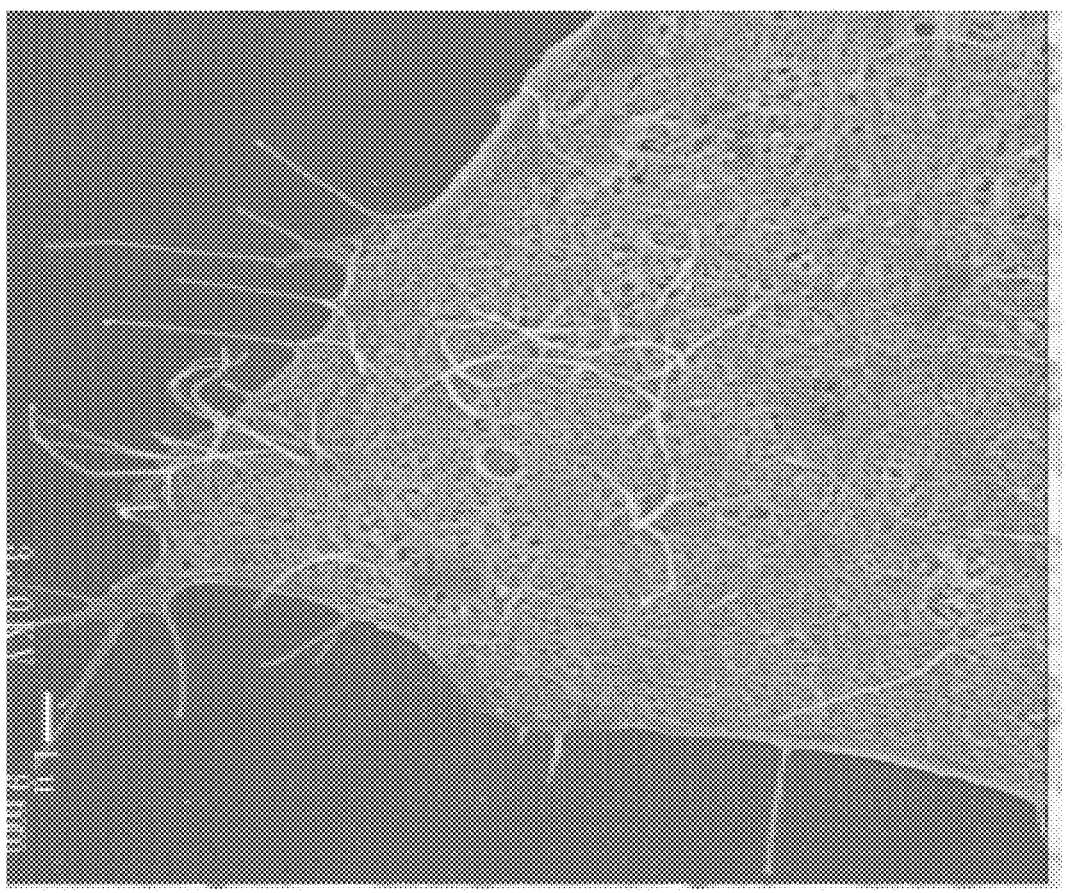

Using Transmission Electron Microscopy, cells transfected with Hath1 and grown to allow for differentiation were visualized. A subset of the cells exhibited distinct hair-like projections. These were the actual hairs from the transfected HNSCs that differentiated into cells having this characteristic feature of IEHCs (FIGS. 5 and 6).

Discussion

In order to replace damaged IEHCs, a renewable source must be created. The HNSCs cultured in serum-free medium were shown to have the ability to become transfected by Hath1 and then differentiate in vitro into IEHCs, or cells having characteristics of IEHCs. In the present example, transfection with and expression of Hath1 appears to be an essential step in the genesis from HNSCs to IEHCs, or cells having characteristics of IEHCs.

Before transfection, HNSCs do not express Hath1. Following transfection with the Neuroporter Kit, they express this gene in their DNA as verified by RT-PCR. They also produce the hair cell specific marker calretinin as verified by immunocytochemistry and Western Blot. Furthermore, actual hairs from the transfected cells can be visualized through electron microscopy. Thus, characteristics of IEHCs are shown by these data, and it appears that these cells either are end-stage IEHCs or are presumptive IEHC cells in that they have at least two characteristics of IEHCs.

Cells expressing IEHC markers and differentiating into cells with hairlike extremities have been generated in this example. These methods, and the cells produced by the methods of the present invention, as shown in this example, advance the art of differentiating multipotent stem cells toward obtaining end-stage neuron-type cells.

Example 2

Introduction

A cholinergic deficit is one of the primary features of Alzheimer's disease (AD), where there is a marked degeneration of long-projecting axons of cholinergic neurons in the basal forebrain and target areas in the hippocampus and cerebral cortex. Recent progress in stem cell technologies suggests the probability of using neuroreplacement strategies in AD therapy, although several hurdles are implicated: i) is it possible to generate large numbers of cholinergic neurons from stem cells; and ii) can long-projecting cholinergic neurons be replaced? Toward improving the ability to conduct research in the area of cell implantation and replacement therapies, and toward achieving desired results in later-developed therapies, embodiments of the present invention are directed to bias human neural stem cells (HNSCs) to differentiate to cells having characteristics of cholinergic neurons through genetic manipulation of endogenous neural precursors in situ.

The LIM-homeobox gene Lhx8 has been reported to be crucial for the proper development of basal forebrain cholinergic neurons in mouse (Zhao et al., 2003; Mori et al., 2004). Lhx8 is expressed in progenitor and postmitotic cells, suggesting that it may have an important role in specification of neural precursor cells and maintenance of phenotype in differentiating and mature neurons. Furthermore, previous studies using the human neuroblastoma cell line, LA-N-2, have demonstrated that treatment with retinoic acid (RA) further enhances cholinergic characteristics of these cells, thus providing a good in vitro model of cholinergic neurons (Crosland, 1996).

The present example utilizes an in vitro assay cell co-culture model with plated RA-differentiated LA-N-2 cells and membrane inserts containing Lhx8-transfected HNSCs, to assess whether the Lhx8-transfected HNSCs adopt a cholinergic neuronal fate. The rationale behind this co-culture model is that HNSCs are influenced by intrinsic as well as extracellular factors in the microenvironment and therefore, able to respond by differentiating into specific cell types according to the environmental cues to which they are exposed. Culture of RA-differentiated LA-N-2 in basal media under a serum-free condition, results in the release of factors to the Lhx8-transfected HNSCs in co-culture. It should be noted that there is no cell-to-cell contact in this co-culture system. Thus it is reasonable to assume that any modification of the cell fate of the genetically modified HNSCs by the cholinergic-differentiated LA-N-2 cells would come from membrane permeable endogenous factor(s) released from the cholinergic-differentiated LA-N-2 cells.

Materials & Method

HNSCs culture: Human NSCs were originally purchased from BioWhittaker, Walkersville, Md. These cells have been expanded and passaged in a serum-free culture medium containing bFGF and EGF in our laboratory for over three years (Brannen & Sugaya, 2000). The HNSCs were cultured at a density of 50 spheres in 75 cm$^2$ culture flasks (Corning, Cambridge, Mass.) in 20 ml of a serum-free supplemented growth medium consisting of HAMS-F12 (Gibco, BRL, Burlington, ON), antibiotic-antimycotic mixture (1:100, Gibco), B27 (1:50, Gibco), human recombinant FGF-2 and EGF (20 ng/ml each, R&D Systems, Minneapolis, Minn.) and heparin (5 µg/ml, Sigma, St. Louis, Mo.) incubated at 37° C. in a 5% $CO^2$ humidified incubation chamber (Fisher, Pittsburgh, Pa.). To facilitate optimal growth conditions, HNSCs were sectioned into quarters every 2 weeks and fed by replacing 50% of the medium every 4-5 days.

LA-N-2 Human Neuroblastoma Culture:

LA-N-2 cells were obtained from Dr. Jan Blusztajn (Boston University, MA). The cells were cultured in Leibovitz L-15 medium (Gibco, BRL, Burlington, ON) containing 10% fetal calf serum and antibiotic-antimyotic mixture (Gibco) in a humidified incubator at 37° C. without CO2. The medium was replaced every 3 days. For treatment with retinoic acid (RA), the cells were sub-plated at a density of 0.5-1×10$^6$ cells/plate using 0.25% trypsin/1 mM EDTA (Gibco, BRL) and allowed to attach overnight. A fresh stock of 4 mM all-trans retinoic acid RA (Sigma, St. Louis, Mo.) was prepared in 100% ethanol under amber lighting. RA solution was diluted into culture media (final concentration. 10$^{-6}$M) and we replaced the media in the cells with the RA-containing media. The media was changed every 48 h during the differentiation of the cells, which was complete after 7-14 days.

Lhx8 Subcloning:

The mouse cDNA clone for Lhx8 (SEQ ID NO: 7, a kind gift from Dr Westphal, NIH, Bethesda, Md.) was inserted into the EcoRI site of the pcDNA 3.1/Zeo mammalian expression vector (Invitrogen). Insertion was subsequently confirmed by restriction digestion and sequence analysis. This mouse Lhx8 (SEQ ID NO: 7) has high homology to the human sequence (70-80%).

Transfection:

HNSCs were placed in 6-well poly-lysine coated plates and transfected with 4 µg pcDNA 3.1/Lhx8 plasmid using the Neuroporter transfection system (Gene Therapy Systems, see description in Example 1). Upon the insertion of the Lhx8 gene expressible sequence into the directional cloning vector, the expressible sequence was operatively linked to the CMV promoter, and was also positioned upstream (with regard to reading) of a polyadenylation transcription termination site. Lhx8 expression was confirmed after 48 hrs by RT-PCR using primers designed from the gene cDNA sequence; 5'TGCTG-GCATGTCCGCTGTCT' 3 (SEQ ID NO: 12, upper primer) and 5'CTGGCTTTGGATGATTGACG'3 (SEQ ID NO: 13, lower primer). To initiate differentiation, HNSCs were placed in serum-free basal medium, and allowed to differentiate for 10-15 days in culture.

Co-Cultures of Transfected HNSCs and RA-Treated LA-N-2 Cells:

HNSCs (~5×10$^4$) transfected with pcDNA 3.1/Lhx8 and non-transfected HNSCs (controls) were transferred into cell culture inserts with an appropriate pore size and suspended in basal media (in the absence of FGF-2 and EGF and without the addition of other extrinsic differentiation factors) over differentiated LA-N-2 cells plated in 6-well plates. For immunocytochemical analyses of HNSCs, the culture insert was removed after 10-20 days of co-culture and the HNSCs were fixed with 4% paraformaldehyde overnight at 4° C. Also, transfected HNSCs were cultured without the presence of differentiated LA-N-2 cells to assess the need for and effectiveness of the co-culturing.

Figure 7:
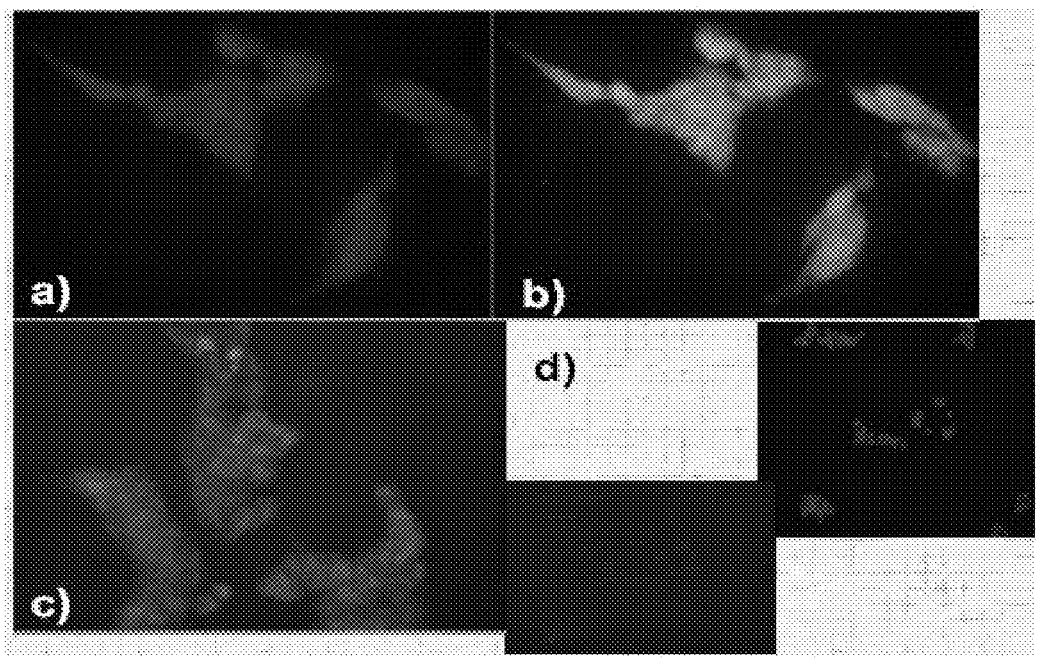

Immunocytochemistry:

Following fixation, HNSCs were briefly washed 3×5 min in Phosphate buffered saline (PBS), then blocked with 3% normal donkey serum in PBS containing 0.05% Tween 20 (PBS-T) and incubated with goat IgG polyclonal anti-human ChAT (1:500, Chemicon), mouseIgG2b monoclonal anti-human βIII-tubulin (1:1000, Sigma) or rabbit anti-human glial filament protein (GFAP) (1:1000, Sigma) overnight at 4° C. The corresponding secondary antibodies (donkey anti-goat, donkey anti-mouse, and donkey anti-rabbit, respectively) conjugated to rhodamine or FITC (Jackson IR Laboratories, Inc.) were added for a 2 hr incubation at RT in the dark. Cells were then washed with PBS (3×5 min) and mounted with Vectashield with DAPI (Vector Laboratories, CA) for fluorescent microscopic observation. LA-N-2 cells were similarly treated to prepare for microscopic observations. Results LA-N-2 cells treated with RA expressed Lhx8, βIII-tubulin, and ChAT. This is demonstrated in FIGS. 7A-D. FIG. 7A shows LA-N-2 cells stained red indicating the presence of βIII-tubulin. FIG. 7B shows LA-N-2 cells stained green indicating the presence of ChAT. FIG. 7C shows LA-N-2 cells stained green indicating the presence of NGF (blue stain indicating counter-staining for nuclei by DAPI). FIG. 7D (insert) shows non-specific staining for ChAT.

In vitro, HNSCs expressing the LIM homeobox gene, Lhx8, differentiated into mainly βIII-tubulin and ChAT-positive cells, in co-culture with LA-N-2 cholinergic cells. For the transfected HNSCs cultured without the presence of differentiated LA-N-2 cells, there was no significant difference from the non-transfected HNSCs with regard to the number of cells differentiating to cells having characteristics of cholingeric cells. This demonstrated the need under these experimental conditions for the differentiated LA-N-2 cells (and the factors released by them).

Non-transfected HNSCs differentiated into mainly βIII-tubulin and GFAP positive cells in co-culture with LA-N-2 cholinergic cells.

With regard to percentage differences between non-transfected cells and transfected cells, in one trial less than two percent of non-transfected cells, and over 40 percent of transfected cells, were observed at the end of the trial to have characteristics of cholinergic neurons.

Conclusions and Comments

Expression of the LIM-homeobox gene Lhx8 triggers HNSCs to adopt a cholinergic neural lineage. Cells having the noted characteristics of cholinergic neurons either are cholinergic neurons or presumptive cholinergic neurons in that they have at least two characteristics of cholinergic neurons.

LA-N-2 cells in co-culture with HNSCs expressing Lhx8, suggest that the microenvironment is also important for the differentiation and survival of cholinergic neurons.

The present invention may provide utility by biasing human neural stem cells through genetically manipulation so that the cells so manipulated may be used in research, including as cells transplantable, such as in experiments, and therapies, including regarding replacing damaged cholinergic neurons.

As to the efficiency of biasing to a desired cell type, and to observing cells having characteristics of a desired end-stage cell type, without being bound to a particular theory, it is believed that the factors that increase the efficiency of biasing by transfection include: 1) inherent properties of the cell to be transfected; 2) inherent efficiency of the selected vector or method of transfection; 3) relative percentage of cells in which the introduced nucleic acid sequence enters the nucleus compared to remains in the cytoplasm; and 4) number of copies of the nucleic acid sequence that are available for expression in the cell. Methods of transfection are well-known in the art, and the use and modification of known approaches to transfection of a cell with a nucleic acid sequence to be expressed therein to improve the percentage of biasing are within the scope of the present invention.

Thus, it is appreciated that in some embodiments of the present invention, a multipotent stem cell is transfected with a desired developmental control gene, and the expression of the gene during in vitro culture biases the differentiation of that cell to a desired end-stage differentiated cell. In other embodiments, the multipotent stem cell may be transfected in vivo with a developmental control gene whose expression biases transfected cells to differentiate into a desired end-stage cell. In any of such embodiments, accessory cells may provide factors that are needed for, or that assist with, the differentiation of the transfected cell. These accessory cells, such as the co-cultured LA-N-2 cells in the above example, need not be in contact with the transfected cells, demonstrating here that the factors are membrane permeable. These factors may include the same factor that is expressed by the transfected gene, or may be other factors known in the art or later determined to be useful in achieving a desired differentiation.

Also, it is appreciated that multipotent stem cells may be cultured without an accessory cell, and may receive factors by direct addition of factors to the culture medium, or such factors may be released by cells at a site of implantation, or may be added to a site of implantation.

Example 3

Using the same vector formation and transfection methods as in Example 2, the Human Lxh8 gene (SEQ ID NO: 6) is transfected into HNSCs. Transfected NHSC cells are cultured in a first treatment that includes LA-N-2 cells that are treated with RA and that express both Lhx8 and ChAT. A co-culture control comprises NHSCs that are not transfected but that are in the same culture vessel as LA-N-2 that are treated with RA and that express both Lhx8 and ChAT. For the first treatment and the co-culture control, HNSC cells are placed in cell culture inserts with an appropriate pore size and suspended in basal media (in the absence of FGF-2 and EGF and without the addition of other extrinsic differentiation factors) over differentiated LA-N-2 cells plated in 6-well plates.

Immunochemistry follows the same procedure as in Example 2 above.

Results indicate that HNSCs transfected with the Human Lxh8 gene (SEQ ID NO: 6) also are predisposed, or biased, to differentiate into cells that have characteristics of cholinergic neurons. Observable results include cells that are positive for βIII-tubulin and ChAT.

Example 4

Figure 8:
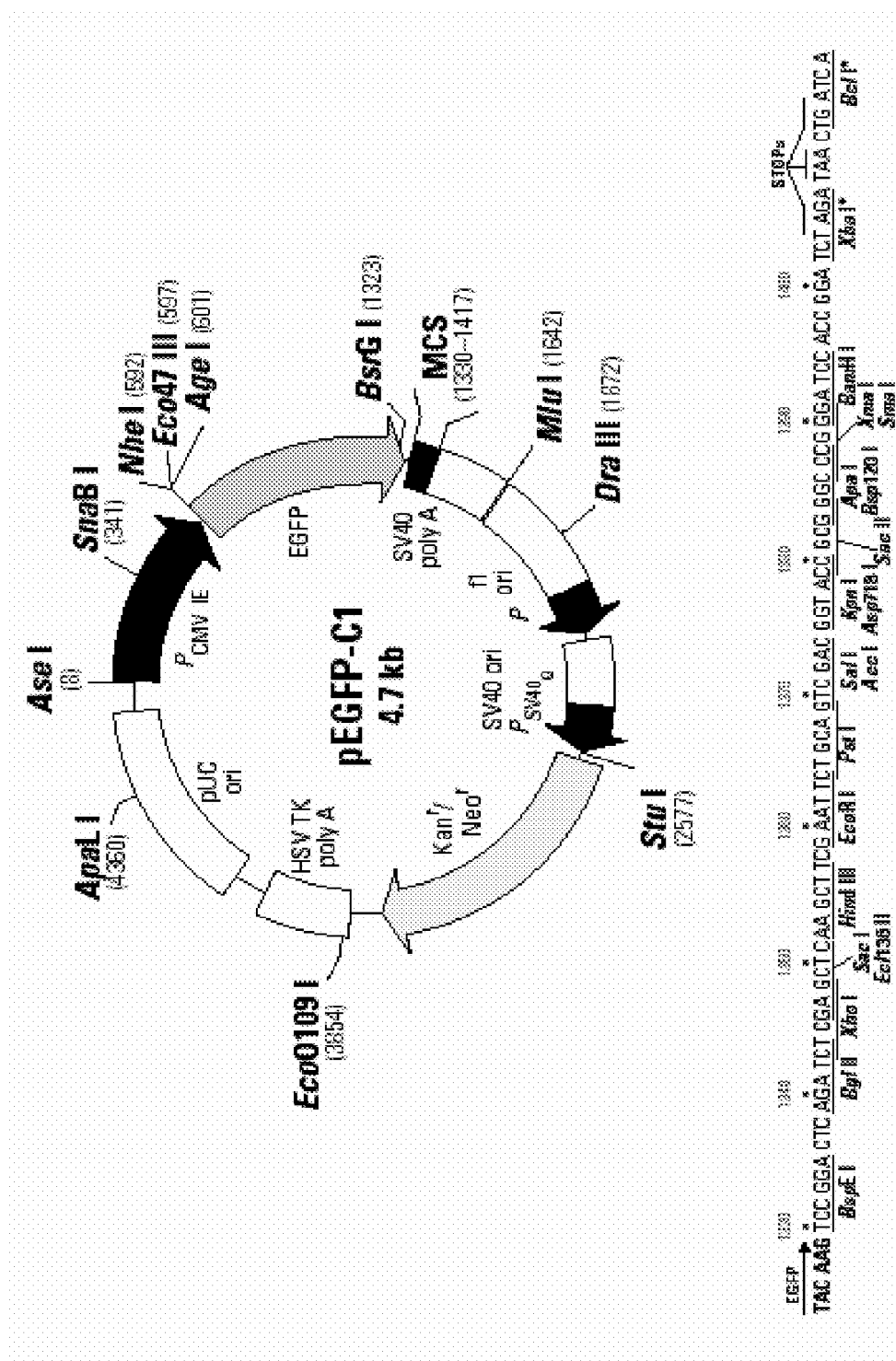
Figure 9:
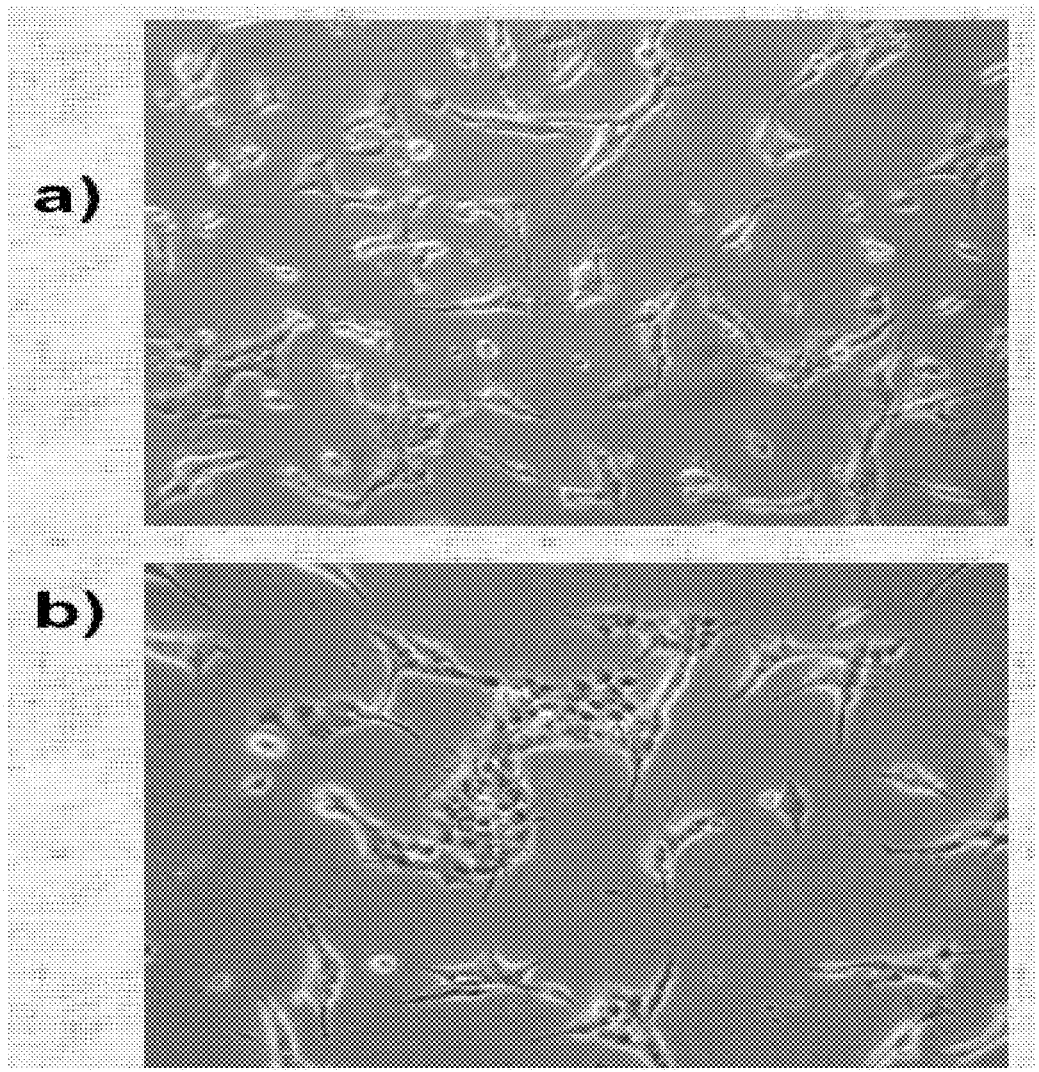
Figure 10:
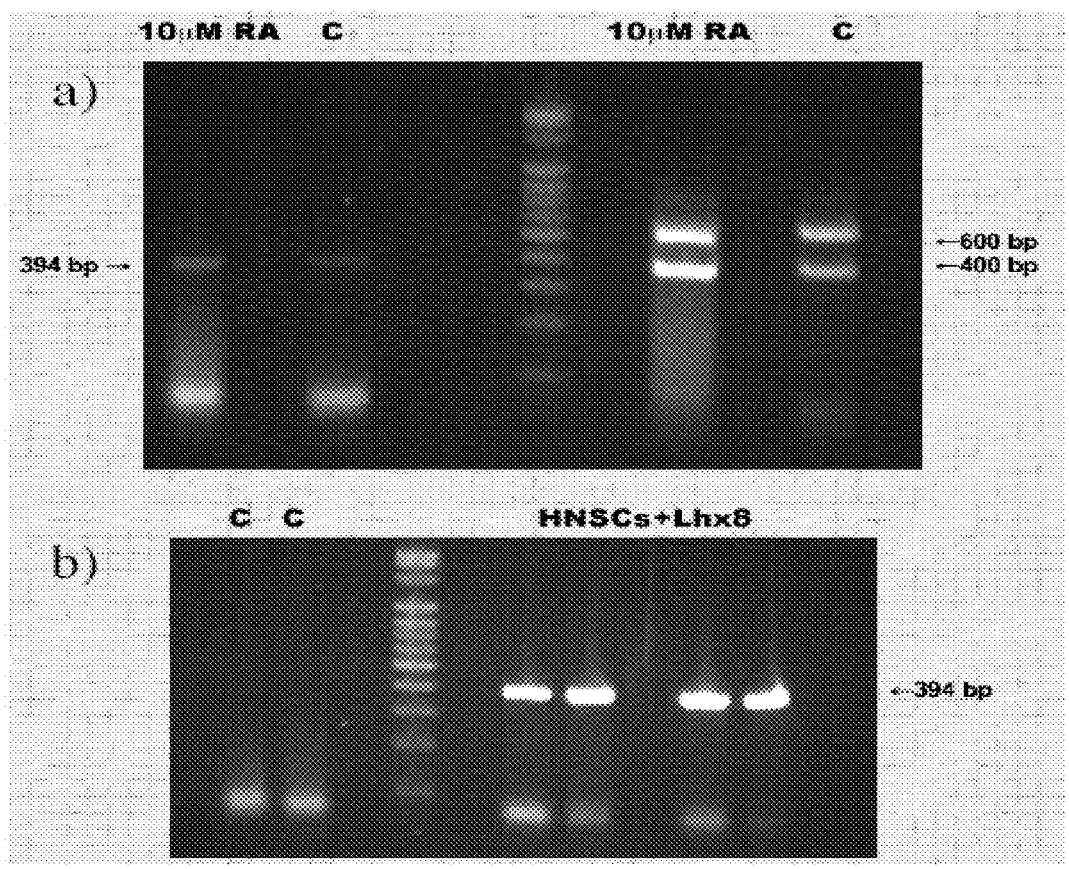
Figure 11:
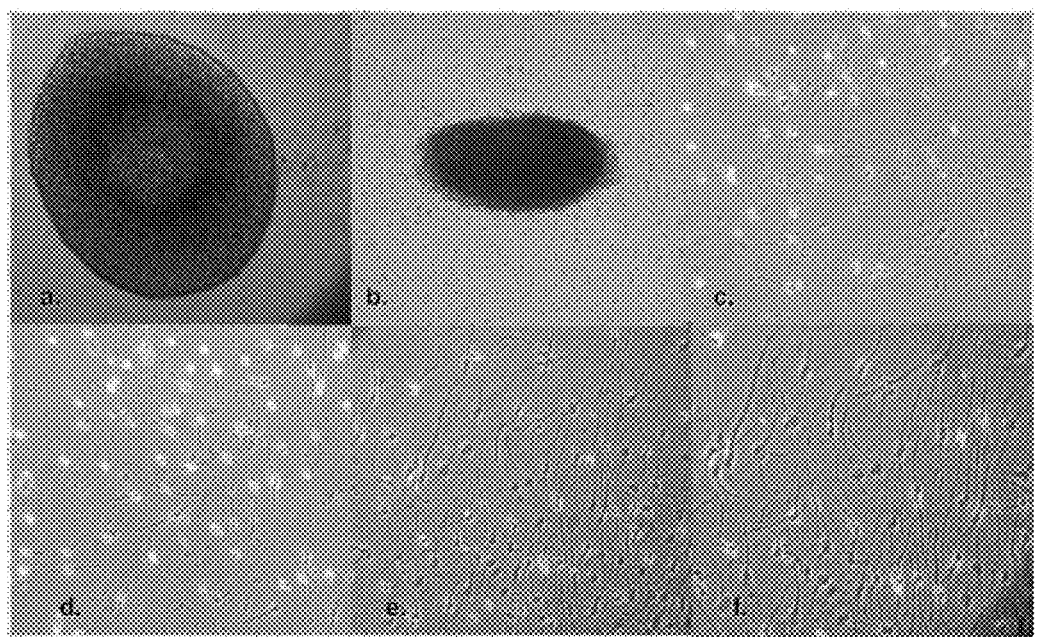
Figure 12:
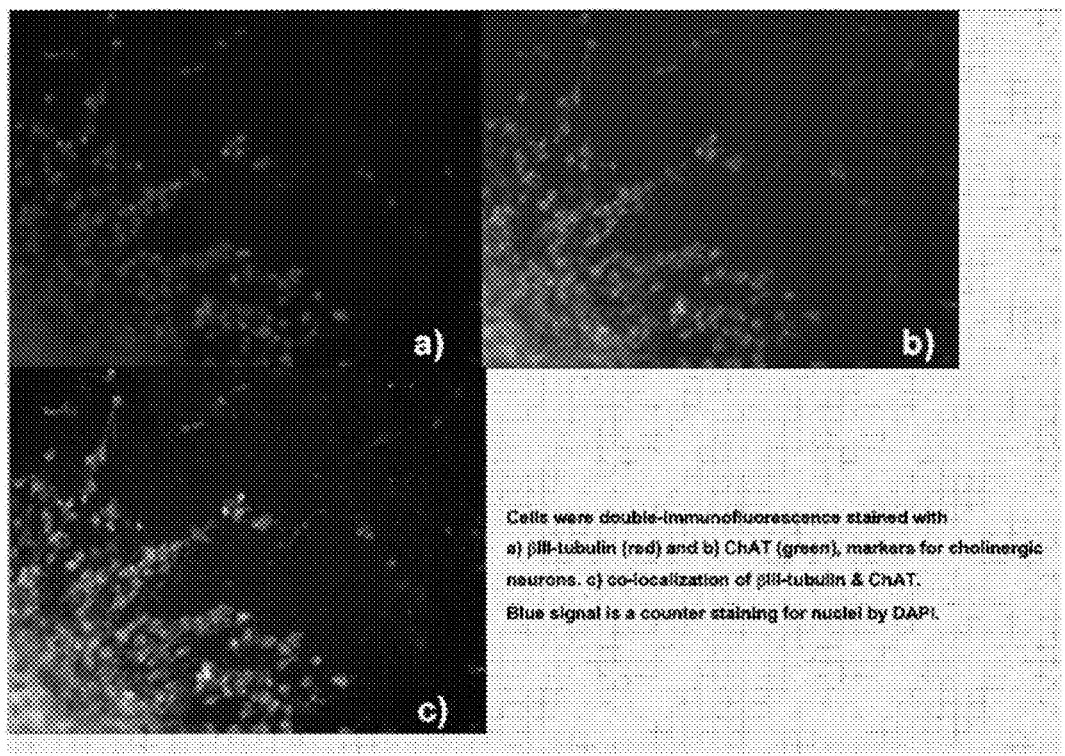
Figure 13:
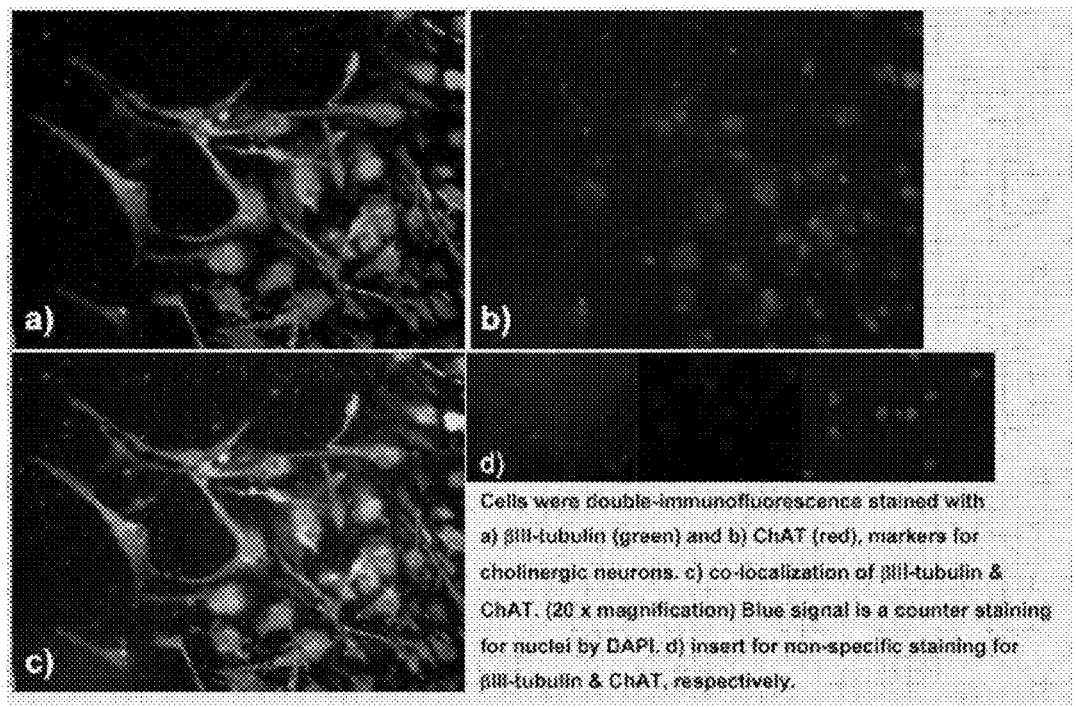
Figure 14:
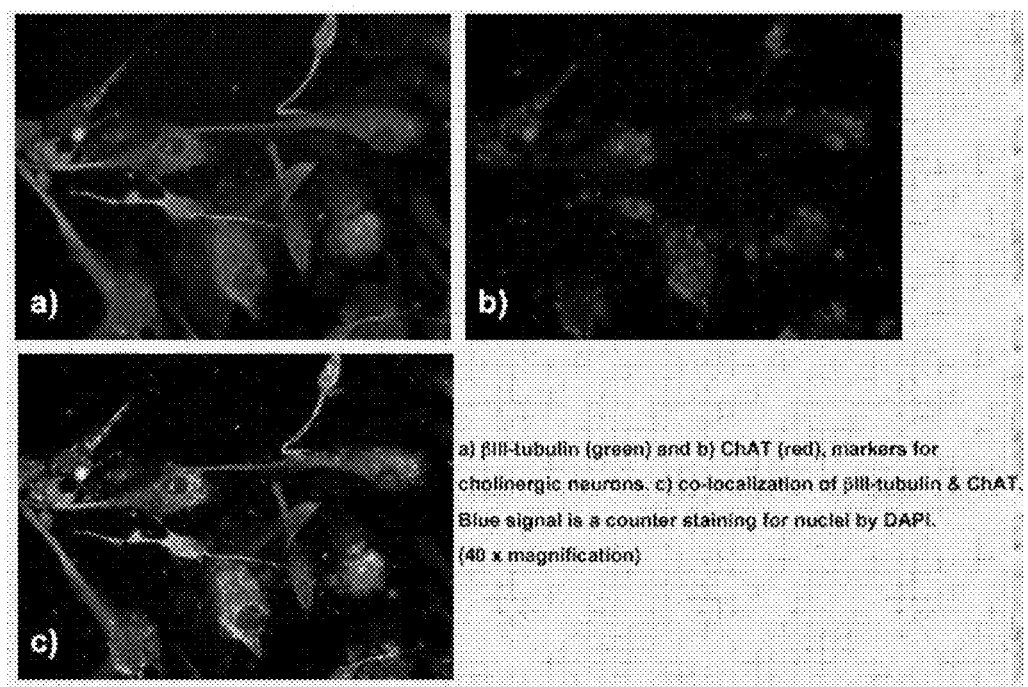
Figure 15:
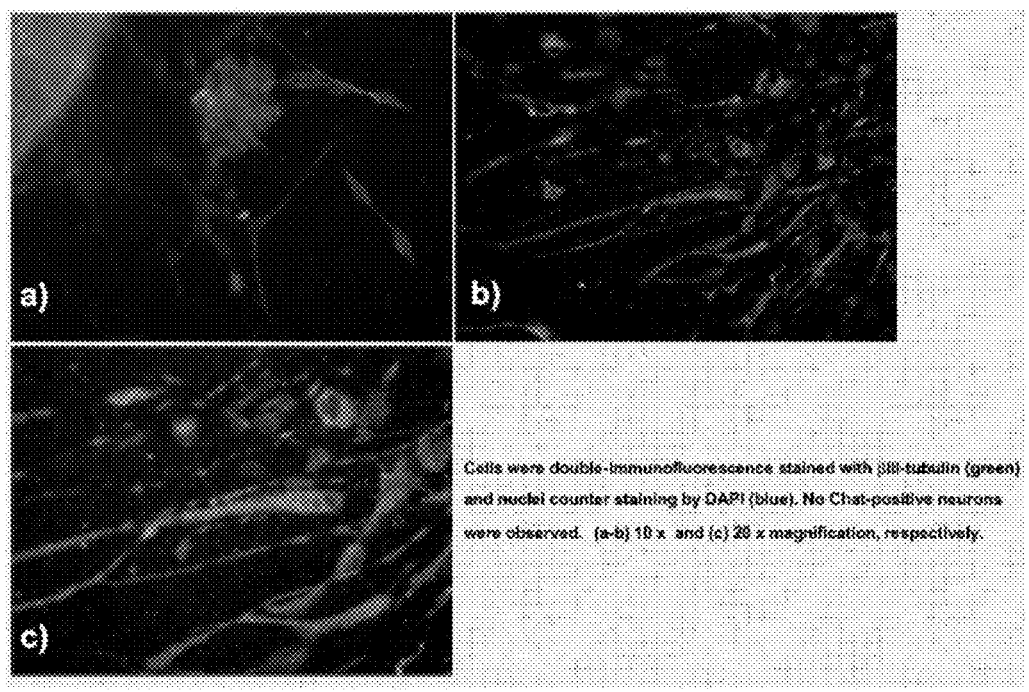
Figure 16:
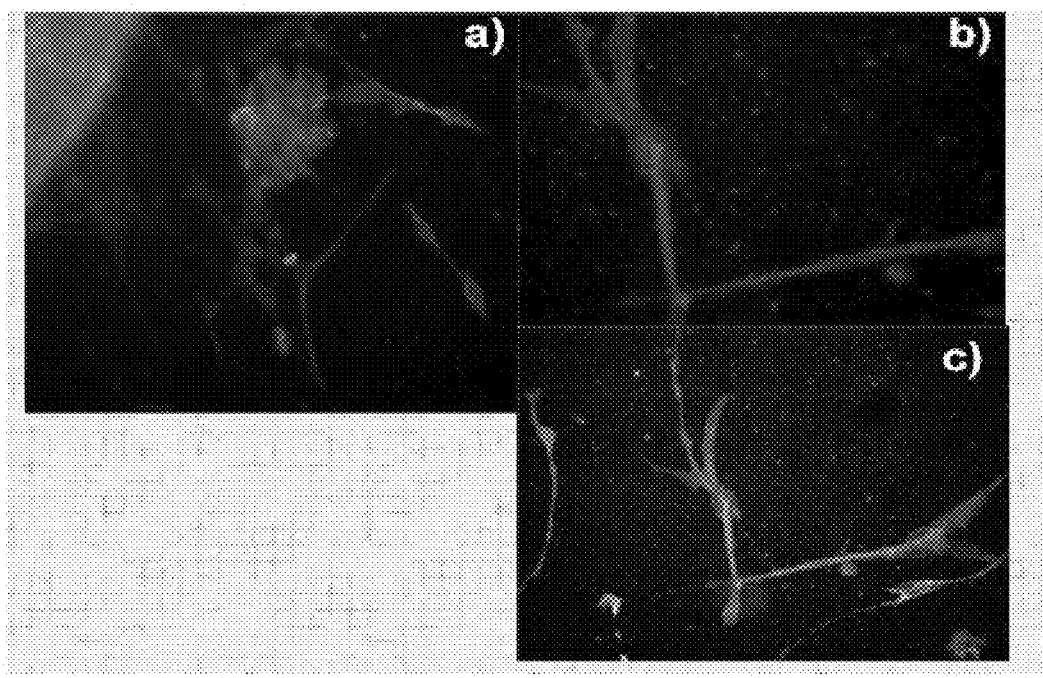

An additional development control gene, Gbx1 sequence (SEQ ID NO: 9), is transfected into HNSCs and is evaluated as to its capacity to bias HNSCs to differentiate to cholingeric cells, or to cells having characteristics of cholinergic cells. The Gbx1 cDNA sequence (SEQ ID NO: 9) is inserted into the enhanced green flouroscent protein (EGFP) vector pEGFP-C1 ((BDBiosciences Clontech) at the EcoRI site within the vector's multiple cloning site, which is 3' of a CMV promoter and the EGFP gene (See FIG. 8; sequence disclosed as SEQ ID NO: 17). Further, in that a question remains as to whether the percentage of biasing is related directly to the percentage of transfection of cells in population of cells exposed to a transfecting vector, the human Lhx8 cDNA (SEQ ID NO:6) independently also is inserted into a second pEGFP-C1 vector. This allows for visualization of both vectors, each bearing an expressible sequence for a different developmental control gene, in cells in respective cell populations into which these vectors are transfected.

Culture methods of the HNSCs into which the Gbx1 and the Lhx8 genes are transfected are as described above in Example 2.

This experiment provides an estimate of the ratio of HNSCs that become cholinergic neurons based on percent transfected of the population. Compared to non-transfected control HNSCs, the transfected cells have characteristics of the desired end-stage differentiated cell type, that is, a cholinergic neuron.

This demonstrates that a number of development control genes, particularly transcription factor genes, may be introduced into a HNSC to bias that cell (or its progeny) to differentiate to a cell having the characteristics of a desired end-stage differentiated neural cell type.

Example 5

Cell sorting technology is combined with the above-described embodiments of the present invention, particularly the vectors of Example 4, to improve the yield and selection of desired cells having the bias to differentiate to a desired end-stage cell (or having already so differentiated). For example, not to be limiting, the introduction of genetic marking such as described above, using EFGP, and the use of Fluorescent Activated Cell Sorter (FACS) techniques is utilized to sort and select cells that have been transfected with the desired developmental control gene (which is linked to a marker on the vector). The FACS technology is well known in the art (See, for example, U.S. patent application number 2002/0127715 A1.)

Using FACS, HNSCs that are transfected with a vector bearing both EFGP and either Gbx1 or Lhx8 are sorted and thereby concentrated. This adds to the utility and effectiveness of the biasing by reducing the number and percentage of cells that are not transfected.

The above examples utilize specific sequences of genes incorporated into respective vectors and introduced into HNSCs. However, the present invention is not meant to be limited to the specifics of these examples. First, in addition to Math1, Hath1, Lxh8 and Gbx1, other developmental control genes of interest include Lhx6, IsL1, Dlx1/2 and Mash. Examples of cDNA sequences, and corresponding translated polypeptide and protein sequences, of these and other developmental control genes are readily obtainable from the GenBank online database (See ncbi.nlm.nih.gov/entrez/query.fcgi.), and these are hereby incorporated by reference for that purpose.

Also, as to the nucleic acid sequences comprising the genes of interest, specific sequences of which are provided in the above examples and in the above paragraph, it is appreciated that substantial variation may exist in a nucleic acid sequence for a gene, yet a polypeptide or protein may nonetheless be produced in a cell from one of a number of such variant nucleic acid sequences, wherein such polypeptide or protein has a desired effect on the cell comparable to a polypeptide or protein produced from one of the nucleic acid sequences specified in the above examples. That is, variations may exist in a nucleic acid sequence for a gene yet the variations nonetheless function effectively when substituted for a nucleic acid sequence of a specified gene.

Accordingly, embodiments of the present invention also include and/or employ nucleic acid sequences that hybridize under stringent hybridization conditions (as defined herein) to all or a portion of a nucleic acid sequence represented by any of the SEQ ID Nos. 1-13, or their complements, or to sequences for IsL1, Dlx1/2, Mash, or their complements. The hybridizing portion of the hybridizing nucleic acid sequences is typically at least 15 (e.g., 20, 25, 30, or 50) nucleic acids in length. The hybridizing portion of the hybridizing nucleic acid sequence is at least 80%, e.g., at least 95%, or at least 98%, identical to the sequence of a portion or all of a nucleic acid sequence encoding one of genes identified by the noted Sequence ID numbers, or one of their complements. Hybridizing nucleic acids of the type described herein can be used, for example, as a cloning probe, a primer (e.g., a PCR primer), or a diagnostic probe, as well as for a gene transfected into a cell as described in the examples above.

Hybridization of the oligonucleic acid probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE).

Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch. Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds), 1995, Current Protocols in Molecular Biology, (John Wiley & Sons, N.Y.) at Unit 2.10.

The above-specified sequences are not meant to be limiting. For example, provided herein are additional identified sequences for Math1 (SEQ ID Nos:2 and 3), and Hath1 (SEQ ID NO:5). Numerous other similar sequences are known and searchable at GenBank. Also, the methods and compositions disclosed and claimed herein for other sequences may be practiced with Gbx1 (SEQ ID NO:9) and sequences similar to it.

Further, the sequences for introduced genes and polypeptides or proteins expressed by them may also be defined in terms of homology to one of the sequences provided in the above examples and discussion. In the context of the present application, a nucleic acid sequence is "homologous" with the sequence according to the invention if at least 70%, preferably at least 80%, most preferably at least 90% of its base composition and base sequence corresponds to the sequence specified according to the invention. According to the invention, a "homologous protein" is to be understood to comprise proteins which contain an amino acid sequence at least 70% of which, preferably at least 80% of which, most preferably at least 90% of which, corresponds to the amino acid sequence disclosed in (Gish and States, 1993); wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc. Thus, a protein may be from 70% up to less than 100% homologous to any one of the proteins expressed by one of the disclosed introduced genes.

Homology, sequence similarity or sequence identity of nucleic acid or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Alternatively, as used herein, "percent homology" of two amino acid sequences or of two nucleic acids is determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleic acid searches are performed with the NBLAST program, score=100, wordlength=12, to obtain nucleic acid sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are used. See ncbi.nlm.nih.gov.

Further, in addition to the homology, as indicated in certain claims (i.e., for some embodiments), is a requirement that the homologous or hybridizable nucleic acid sequence or polypeptide or protein functions analogously to the specified sequence of which it is homologous or with which it is hybridizable. That is, the homologous or hybridizable variant functions to achieve the same result, i.e., to increase the probability of a transfected cell, or the percentage of a number of cells, that are biased to differentiate to a cell, or cells, respectively, having characteristics of a desired end-stage differentiated cell.

While the transfection into HNSCs in the above examples uses the Neuroporter approach (Gene Therapy Systems, Inc. San Diego, Calif.), it is appreciated that any known or later-developed method of introduction of a nucleic acid sequence may be employed in the methods and systems, and to produce the compositions, of the present invention. For example, and not to be limiting, introduction of a nucleic acid sequence may be effectuated by stable or transient transfection, lipofection by methods other than Neuroporter, calcium phosphate treatment, electroporation, infection with a recombinant viral vector, and the use of vectors comprising a plasmid construct. Generally and collectively, these methods are considered to be included in the term "means to transfect," in the term "step for transfecting." Also, the use of the particular promoter and polyadenylation transcription termination site are not meant to be limiting, as many promoter and transcription termination sites are known and used routinely in the art.

As to the use of different means to transfect, and in view of the above discussion of the relative percentage of cells biased to cells having characteristics of a desired end-stage cell type, it is appreciated that types of transfection, cells that are transfected, and other factors, including post transfection conditions, affect the percentage of cells ultimately biased. In view of these factors, and considering the importance of the specific developmental control genes that are introduced to a cell in certain embodiments of the present invention, in some embodiments the percentage of transfected cells biased exceeds 40 percent, in other embodiments the percentage of transfected cells biased exceeds 50 percent, in other embodiments the percentage of transfected cells biased exceeds 65 percent, and in other embodiments the percentage of transfected cells biased exceeds 70 percent. However, it also is appreciated that determination of the percentage of cells that are in fact transfected in a given container of cells may be difficult to assess, the performance of the present invention in certain embodiments may be expressed in an alternative manner. That is, in some embodiments of the present invention in which a number of cells has been exposed to a selected method or means of transfection for the purpose of introducing a desired developmental control gene (such as Lhx8), the percentage of total cells that are biased to a desired end-stage cell type, or to a cell having characteristics of a desired end-stage cell type, is at least 35 percent, in other embodiments such percentage of total cells exceeds 50 percent, and in other embodiments such percentage of total cells exceeds 70 percent.

Further, it is appreciated that embodiments of the present invention are described as follows:

1. A neural stem cell, including a human neural stem cell, comprising an introduced nucleic acid sequence having an expressible developmental control gene, the expression of said gene being effective to increase the probability of differentiation of said cell to a desired neural cell type.
2. A neural stem cell, including a human neural stem cell, comprising an introduced nucleic acid sequence having an expressible developmental control gene, the expression of said gene being effective to increase the probability of differentiation of said cell to a cell having characteristics of a cholinergic neuron.
3. A neural stem cell, including a human neural stem cell, comprising an introduced nucleic acid sequence having an expressible developmental control gene, the expression of said gene being effective to increase the probability of differentiation of said cell to a cell having characteristics of an inner ear hair cell.

4. A neural stem cell, including a human neural stem cell, comprising an introduced nucleic acid sequence having an expressible developmental control gene, the expression of said gene being effective to increase the probability of differentiation of said cell to a cell having characteristics of a dopaminergic neuron.

The developmental control gene in the above first description of embodiments of the present invention may be selected from the group consisting of Math1, Hath1, Lhx8, Gbx1, Lhx6, IsL1, Dlx1/2, Mash and Nurr1. The developmental control gene in the above second description of embodiments of the present invention may be selected from the group consisting of Lhx8, Gbx1, Lhx6, IsL1, Dlx1/2, and Mash. The developmental control gene in the above third description of embodiments of the present invention may be selected from the group consisting of Math1 and Hath1. Finally, the developmental control gene in the above fourth description of embodiments of the present invention may be Nurr1, Pitx3 (SEQ ID NO: 13) or other later-identified specific genes.

Also, it is appreciated that the present invention, particularly for the genes Math1, Hath1, Lhx8, Gbx1, Lhx6, IsL1, Dlx1/2, and Mash, may be utilized in potent cells, that is, in cells that are considered to fall within the definitions of pluripotent, of multipotent, and of progenitor cells (i.e., more differentiated than multipotent yet capable of limited self-renewal).

Based on the above examples and disclosure, in view of the knowledge and skill in the art, it also is appreciated that embodiments of the present invention also are used for any homeobox gene, so that a homeobox gene is transfected to a stem cell to effect a biasing of the stem cell to differentiate to a desired end-stage cell, or to a cell having characteristics of the end-stage cell. The stem cell may be a pluripotent or a multipotent stem cell; alternatively invention embodiments transfecting homeobox genes may be practiced with progenitor cells as described herein. Cells so biased by these genes following the methods of the present invention also are considered to fall within the scope of embodiments of the present invention.

Example 6

Nkx2-5 Biases the Differentiation Toward the Development of Cardiac Cells

According to another embodiment, transfection with Nkx2-5 (SEQ ID NO: 12) biases the differentiation toward the development of cardiac cells. See FIG. 17. Red=human specific Troponin I, Green=Human cells. Following transfection, multipotent stem cells were cocultured with rat cardiomyocytes that provide environmental signals to allow the transfected cells to develop properly.

Further, and more generally, embodiments of the present invention may be practiced by transfecting a stem or a progenitor cell with a nucleic acid sequence comprising a development control gene, so that the transfecting is effective to bias the cell to differentiate to a desired end-stage cell, or to a cell having characteristics of the end-stage cell.

Also, it is appreciated that the methods of the present invention may be applied to the daughter cells of multipotent cells, which may have begun some stages of differentiation but are still capable of being biased by transfection of appropriate developmental control genes as described herein, but by virtue of initiating differentiation (or being less self-renewing) may by some opinions therefore not be considered to be multipotent cells. For the purposes of this invention, such daughter cells, which may be found in culture with the multipotent stem cells from which they arose, are termed "biasable progeny cells."

It is appreciated that embodiments of the present invention also may be defined and claimed with regard to the polypeptide or protein sequences expressed as a result of the transfections disclosed and discussed above. For example, not to be limiting, the peptide sequences, disclosed as the translation sequences in the attached Sequence Listing pages, and their expression in a transfected cell, are used to identify and/or characterize a characteristic and/or result of embodiments of the present invention. Translation sequences are obtainable from the respective GenBank database data entries for cDNAs as described herein, and those database entries are incorporated by reference for such information.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method of biasing differentiation of a neural stem cell comprising introducing an expression construct comprising a Hath1 gene sequence into the neural stem cell in vitro, wherein expression of the Hath1 gene sequence is effective to bias the neural stem cell to a desired end-stage cell type, in vitro, wherein the desired end-stage cell type comprises characteristics of an inner-ear hair cell, the characteristics comprising inner ear hair cell projections.

2. A method of biasing differentiation of a neural stem cell in vitro comprising:
   a. providing the neural stem cell;
   b. preparing a nucleic acid sequence comprising a promoter operatively linked to an expressible sequence that comprises a Hath1 gene sequence, the nucleic acid sequence comprising a transcription termination site; and
   c. transfecting said neural stem cell with said nucleic acid sequence, in vitro;
   wherein expression of the expressible sequence results in biasing the neural stem cell to a desired end-stage cell type, in vitro, wherein the desired end-stage cell type comprises characteristics of an inner-ear hair cell, the characteristics comprising inner ear hair cell projections.

3. A method of biasing differentiation of one or more cells in a population of cells comprising neural stem cells, comprising:
   a. providing the population of cells in a vessel;
   b. adding to the vessel a plurality of copies of a nucleic acid sequence comprising Hath1 gene sequence under conditions to express said gene sequence;
   wherein expression of the gene sequence in one or more cells transfected, in vitro, with a copy of the nucleic acid sequence is effective to bias the one or more cells to a desired end-stage cell type, wherein the desired end-stage cell type comprises characteristics of an inner-ear hair cell, the characteristics comprising inner ear hair cell projections.

4. The method of claim 3, the population of cells additionally comprising one or more biasable progeny cells.

5. The method of claim 3, the neural stem cells comprising human neural stem cells.

* * * * *